(12) United States Patent
Tsien et al.

(10) Patent No.: US 7,427,680 B2
(45) Date of Patent: *Sep. 23, 2008

(54) FLUOROGENIC SUBSTRATES FOR BETA-LACTAMASE GENE EXPRESSION

(75) Inventors: Roger Y. Tsien, La Jolla, CA (US); Jianghong Rao, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 10/884,019

(22) Filed: Jul. 2, 2004

(65) Prior Publication Data

US 2005/0118669 A1 Jun. 2, 2005

Related U.S. Application Data

(63) Continuation-in-part of application No. 10/044,486, filed on Jan. 11, 2002.

(60) Provisional application No. 60/261,313, filed on Jan. 12, 2001.

(51) Int. Cl.
*C07D 501/24* (2006.01)
*G01N 33/573* (2006.01)

(52) U.S. Cl. .................................. 540/222; 435/173.2

(58) Field of Classification Search ........................ None
See application file for complete search history.

(56) References Cited

U.S. PATENT DOCUMENTS 3,891,635 A 6/1975 Henniger et al.

(Continued)

FOREIGN PATENT DOCUMENTS

EP 0 553 741 A2 8/1993

(Continued)

OTHER PUBLICATIONS

Farina, Stephen R. Baker, Daniel A. Benigni, Sheila I. Hauck, and Chester Sapino, J. Org. Chem.; 1990; 55(23) pp. 5833-5847.*

(Continued)

*Primary Examiner*—Mark L Berch
(74) *Attorney, Agent, or Firm*—Quine Intellectual Property Law Group; Gary Baker

(57) ABSTRACT

Fluorescent substrates for beta-lactamases having the general formula shown above are provided. Z includes a fluorophore or chromophore and includes a group that may link to the lactam-containing group; $R_1$ and $R_2$ are independently selected from H, aliphatic, aromatic, alkyl, and acyl; $R_4$ may be H and lower alkyl; B may be H, physiologically acceptable salts or metal, ester groups, ammonium cations, —$CHR_5OCO(CH_2)_nCH_3$, —$CHR_5OCOC(CH_3)_3$, acylthiomethyl, acyloxy-alpha-benz, deltabutyrolactonyl, methoxycarbonyloxymethyl, phenyl, methylsulphinylmethyl, beta-morpholinoethyl, dialkylaminoethyl, and dialkylaminocarbonyloxymethyl, in which $R_5$ is selected from the group consisting of H and lower alkyl; n is an integer between 0 and 10, inclusive; and A may be S, O, SO, $SO_2$ or $CH_2$. In embodiments, the beta-lactam ring may be cleaved by a beta-lactamase enzyme effective to free a fluorophore. Methods of assaying beta-lactamase activity and monitoring expression in systems using beta-lactamase as a reporter gene are also disclosed.

Formula 1

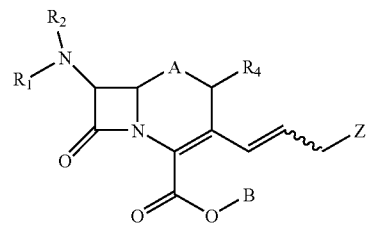

11 Claims, 13 Drawing Sheets

U.S. PATENT DOCUMENTS

| | | | |
|---|---|---|---|
| 3,991,051 A | | 11/1976 | Breuer et al. |
| 4,074,047 A | * | 2/1978 | Foxton et al. ............... 540/224 |
| 4,177,189 A | | 12/1979 | Akkerboom et al. |
| 4,486,586 A | * | 12/1984 | Narita et al. ................ 540/222 |
| 4,740,459 A | | 4/1988 | Chen et al. |
| 4,751,285 A | * | 6/1988 | Toohey ....................... 530/331 |
| 4,758,556 A | * | 7/1988 | Durckheimer et al. ...... 514/206 |
| 5,075,298 A | * | 12/1991 | Aszodi et al. ............... 514/206 |
| 5,338,843 A | * | 8/1994 | Quante et al. ............... 540/222 |
| 5,416,080 A | * | 5/1995 | Aszodi et al. ............... 514/206 |
| 5,541,318 A | * | 7/1996 | Aszodi et al. ............... 540/222 |
| 5,741,657 A | * | 4/1998 | Tsien et al. ................. 540/222 |
| 5,948,484 A | * | 9/1999 | Gudimenko et al. ........ 427/489 |
| 5,955,604 A | * | 9/1999 | Tsien et al. ................. 540/222 |
| 6,197,223 B1 | * | 3/2001 | Weaver et al. ............... 252/582 |
| 6,846,612 B2 | * | 1/2005 | Deshpande .............. 430/271.1 |
| 2005/0227309 A1 | * | 10/2005 | Corry et al. .................... 435/32 |
| 2006/0046173 A1 | * | 3/2006 | Sakai et al. .............. 430/108.1 |
| 2007/0020715 A1 | * | 1/2007 | Tsien et al. .................... 435/18 |

FOREIGN PATENT DOCUMENTS

WO     WO 2005/071096 A2    8/2005

OTHER PUBLICATIONS

Anderson and Pratt (1981) "Pre-Steady State β-Lactamase Kinetics." *The Journal of Biological Chemistry*, 256(22): 11401-11404.

Cavrois et al. (2002) "A sensitive and specific enzyme-based assay detecting HIV-1 virion fusion in primary T lymphocytes." *Nature Biotechnology*, 20: 1151-1154.

Chang et al. (1990) "Altering enzymatic activity: Recruitment of carboxypeptidase activity into an RTEM β-Lactamase/penicillin-binding protein 5 chimera." *Proceedings of the National Academy of Sciences*, USA, 87: 2823-2827.

Christensen and Salzmann (1983) "Strategy in the Total Synthesis of β-Lactam Antibiotics." In: *Handbok of Experimental Pharmacology*. vol. 67/I. Springer-Verlag, Berlin, Chapter 11; pp. 329-354.

Durckheimer et al. (1987) "Synthesis and Biological Properties of Newer Cepem Antibodies." *Fontiers of Antibiotic Research*, ed. Umezawa, Academic Press, Tokyo, pp. 161-192.

Ernest (1982) "The Penems." *Chemistry and biology of Beta-Lactam Antibiotics*, vol. 2. Nontraditional Beta-Lactam Antibiotics, ed Morin et al., Academic Press, New York., Chapter 5: 315-360.

Galarneau et al. (2002) "β-Lactamase protein fragment complementation assays as in vivo and in vitro sensors of protein-protein interations." *Nature Biotechnology*, 20: 619-622.

Gao et al. (2003) "Novel Fluorogenic Substrates for Imaging β-Lactamase Gene Expression." *Journal of the American Chemistry Society*, 125: 11146-11147.

Heusler (1972) "Total Synthesis of Penicillins and Cephalosporins." In: *Cephalosporins and Penicillins: Chemistry and Biology*, ed Flynn, Academic Press, New York., Chapter 6: pp. 255-280.

Jones et al. (1982) "In Vitro Evaluation of Pyridine-2-Azo-p-Dimethylaniline Cephalosporin, a New Diagnostic Chromogenic Reagent, and Comparison with Nitrocefin, Cephacetrile, and Other Beta-Lactam Compounds." *Journal of Clinical Microbiology*, 15(4): 677-683.

Kadonaga et al. (1984) "The Role of the β-Lactamase Signal Sequence in the Secretion of Proteins by *Escherichia coli*." *Journal of Biological Chemistry*, 259(4): 2149-2154.

Koster et al. (1982) "Monobactams." *Chemistry and Biology of Beta-Lactam Antibiotics*, ed. vol. 3, Morin et al., Academic Press, New York., Chapter 7: 339-378.

Matagne et al. (1998) "Catalytic properties of class a β-Lactamase: efficiency and diversity." *Biochemical Journal*, 330: 581-598.

Moore et al. (1997) "The Development of β-Lactamase as a Highly Versatile Genetic Reporter for Eukaryotic Cells." *Analytical Biochemistry*, 247(2): 203-209.

O'Callaghan et al.(1972) "Novel Method for Detection of β-Lactamases by Using a Chromogenic Cephalosporin Substrate." Antimocrobial Agents and Chemotherapy p. 283-288.

O'Callaghan et al. (1968) "Effects of β-Lactamase from Gram-negative Organism on Cephalosporins and Penicillins." *Antimicrobial Agents and Chemotherapy*, 8: 57-63.

Phlippon et al. (1998) "The diversity, structure and regulation of β-lactamase." *Cellular and Molecular Life Sciences*, 54(4): 341-346.

Prasanna De Silva et al. (1999) "Emerging fluorescence sensing technologies: From photophysical principles to cellular applications." *Proceedings of the National Academy of Sciences*, USA, 96: 8336-8337.

Spotts et al. (2002) "Time-lapse imaging of a dynamic phosphorylation-dependent protein-protein interaction in mammalian cells." *Proceedings of the National Academy of Sciences*, USA, 99(23): 15142-15147.

Stratton (1988) "Activity of β-Lactamase against β-lactams." *The Journal of Antimicrobial Chemotherapy*, 22(Suppl. A): 23-35.

Stryer (1981) "Introduction to Enzymes." In: *Biochemistry*, New York: W. H. Freeman and company, Chapter 6: pp. 103-134.

Sutcliffe (1978) "Nucleotide sequence of the ampicillin resistance gene of *Escherichia coli* plasmid pBR322." *Proceedings of the National Academy of Sciences*, USA, 75: 3737-3741.

Wehrman et al. (2002) "Protein-protein interactions monitored in mammalian cells via complementation of β-Lactamase enzyme fragments." *Proceedings of the National Academy of Sciences*, USA, 99(6): 3469-3474.

Whitney et al. (1998) "A genome-wide functional assay of signal transduction in living mammalian cells." *Nature Biotechnology*, 16: 1329-1333.

Zlokarnik et al. (1998) "Quantitation of Transcription and Clonal Selection of Single Living Cells with β-Lactamase as Reported." *Science*, 279(2): 84-88.

Zlokarnik (2000) "Fusions to β-lactamase as a reporter for gene expression in live mammalian cells." *Methods in Enzymology*, 326: 221-241.

\* cited by examiner

INCREASED RESORUFIN DEPOSITION IN β-LACTAMASE-TRANSFECTED vs. WILD TYPE CELLS

BLA-TRANSFECTED C6 GLIOMA CELLS

WT C6 GLIOMA

CEPHALOSPORIN-PHENOL ETHERS

Preferred R = benzyl, 2-thienylmethyl, or cyanomethyl; A = S or SO; R' = H or physiologically acceptable salts or ester groups.

Where Z can be:

Where X = H, F, Cl, Br, $CO_2R'$; Y = N, CH, C-CN, C-CF$_3$

CR2: R = H    CR2/AM: R = CH₂OCCH₃

FLUOROGENIC SUBSTRATES FOR BETA-LACTAMASE GENE EXPRESSION

CROSS-REFERENCE TO RELATED APPLICATIONS

This application is a continuation-in-part of U.S. patent application Ser. No. 10/044,486, filed Jan. 11, 2002, from which priority is claimed under 35 U.S.C. § 120, and claims the benefit under 35 U.S.C. § 119(e) of U.S. Provisional Application Ser. No. 60/261,313, filed Jan. 12, 2001, the entire contents of each of which applications is hereby incorporated by reference herein.

GOVERNMENT INTERESTS

This invention was made in part with government support under Grant Nos. NIH NS27177 and DOE DE-FG03-01ER63276. The government has certain rights in this invention.

BACKGROUND OF THE INVENTION

Field of the Invention

The present invention relates generally to the fields of chemistry and biology. More particularly, the present invention relates to compounds that are substrates for beta-lactamase activity and methods for their use in measuring beta-lactamase activity.

Beta-lactamases are a family of bacterial enzymes that cleave penicillins and cephalosporins with high catalytic efficiency and render these bacteria resistant to β-lactam antibiotics (Bush, K.; Sykes, R. B. in *Antimicrobial Drug Resistance* (Bryan, L. E., Ed.) 1984, pp 1-31, Academic Press, New York.) Rapid and sensitive detection of β-lactamase activity in biological samples is thus of large clinical importance. While β-lactamases are the biochemical markers for identification of β-lactam antibiotics-resistant bacterial pathogens, the β-lactamase activity can also serve as a "reporter" or "sensor" for monitoring biological processes and interactions of interest (see, e.g., Tsien et al. U.S. Pat. No. 6,031,094).

A reporter gene assay measures the activity of a gene's promoter, and thus the expression of the proteins encoded by the gene or genes that are under the control of the promoter. These proteins can be involved in a variety of cellular activities. Therefore, a reporter gene assay also measures cellular activities associated with the proteins. These assays generally use techniques in molecular biology to make nucleic acid constructs that place a gene under the control of a promoter. These constructs can then be stably or transiently introduced into a cell, such as a mammalian cell (see, Gorman, C. M. et al,. Mol. Cell Biol. 2: 1044-1051 (1982); and Alam. J. and Cook, J. L., Anal.Biochem. 188: 245-254, (1990)). When the promoter is activated, the reporter gene is expressed and a reporter protein is produced. The reporter protein can be, for example, an enzyme that converts a substrate into a detectable product. The product can be measured qualitatively or quantitatively as a measure of the activation of the promoter and thus the level of activity of the genes normally under the control of that promoter.

Several reporter genes are known in the art and some are commercially available (see, Alam and Cook, supra). The reporter gene can be inserted within a plasmid that is particularly suited for an organism and molecular biology manipulations. Promoters of interest can be inserted into cloning sites so that the expression of the reporter gene is under the control of the promoter (see, Rosenthal, N., Methods Enzymol. 152: 704-720 (1987); and Shiau, A. and Smith, J. M., Gene 67: 295-299 (1988)). Known methods are used to introduce these plasmids into a cell type or whole organism (see, Sambrook et al., Molecular Biology, A Laboratory Manual, Cold Spring Harbor Laboratory Press (1989); and Nolan, In: Molecular Cloning, Cold Spring Harbor Laboratory Press, (1989)). The plasmids can also encode a resistance marker, such as resistance to antibiotics so that successfully transfected cells can be selected, identified, and cultured.

TEM-1 β-lactamase (Bla), the 29 kDa isoform product of the ampicillin resistance gene (amp'), is an especially useful reporter because it is relatively small and monomeric, does not exist in eukaryotes but can be easily expressed in eukaryotic cells without any noticeable toxicity. (Matagne, A.; Lamotte-Brasseur, J.; Frere, J. M. *Biochem. J.* 1998, 330, 581-598; Phlippon, A.; Dusart, J.; Joris, B.; Frere, J. M. *Cell Mol. Life Sci.* 1998, 54, 341-346.) TEM-1 Bla has been developed as a reporter for examining the promoter/regulatory elements activity in living mammalian tissue culture cells. (Zlokarnik, G.; Negulescu, P. A.; Knapp, T. E.; Mere, L.; Buttes, N.; Feng, L.; Whitney, M.; Roemer, K.; Tsien, R. Y. Science 1998, 279, 8488; Zlokarnik, G. *Methods in Enzymology* 2000, 326, 221-241; Whitney, M.; Rockenstein, E.; Cantin, G.; Knapp, T.; Zlokarnik, G.; Sanders, P.; Durick, K.; Craig, F. F.; Negulescu, P. A. *Nat. Biotech.* 1998, 16, 1329-1333) Protein fragment complementation assays based on Bla have been successfully applied to monitor constitutive and inducible protein interactions both in vitro and in vivo (Galarneau, A.; Primeau, M.; Trudeau, L.-E.; Michnick, S. W. *Nat. Biotech.* 2002, 20, 619-622; Wehrman, T.; Kleaveland, B.; Her, J.-H.; Balint, R. F.; Blau, H. M. *Proc. Natl. Acad. Sci. USA* 2002, 99, 3469-3474; Spotts, J. M.; Dolmetsch, R. E.; Greenberg, M. E. *Proc. Natl. Acad. Sci. USA* 2002, 99,15142-15147). Incorporation of Bla into HIV-1 virions allows convenient detection of HIV-1 virion fusion in primary T lymphocytes in complex cell populations. (Cavrois, M.; de Noronha, C.; Greene, W. C. *Nat. Biotech.* 2002, 20, 1151-1154).

Substrates for enzymatic reporter proteins can be chromogenic or fluorescent. In some assays, a fluorescent substrate changes fluorescence properties upon conversion by the reporter enzyme to a fluorescent product. Preferably, a fluorescent product is highly fluorescent and can become trapped within the cell rather than being detectable in the media surrounding the cells. These features allow the expression of the reporter protein to be monitored and measured in individual cells rather than in a population of cells (see, WO 96/30540 to Tsien, published Oct. 3, 1996).

Substrates that detect Bla activity with high sensitivity are critical for the successful implementations of Bla assays. Fluorogenic substrates are superior to chromogenic substrates, such as well-known nitrocefin and PADAC (O'Callaghan, C. H.; Morris, A.; Kirby, S. M.; Shingler, A. H. *Antimicrob. Agents Chemother.* 1972, 1, 283-288; Jones, R. N.; Wilson, H. W.; Novick, W. J. Jr. *J. Clin. Mcrobiol.* 1982, 15, 677-683; Moore, J. T.; Davis, S. T.; Dev, I. K. *Anal. Biochem.* 1997, 247, 203-209) in detecting enzyme activity because of the high sensitivity of fluorescence detection. The first reported fluorogenic Bla substrate shown to work with cells was CCF2, which consists of a donor 7-hydroxycoumarin linked via a cephalosporin to an acceptor fluorescein.[4] CCF2 fluoresces green because of fluorescence resonance energy transfer from the coumarin donor to the fluorescein acceptor. Hydrolysis of the cephalosporin by Bla splits off the fluorescein, disrupts energy transfer, and shifts the emission to blue (Zlokarnik, G.; Negulescu, P. A.; Knapp, T. E.; Mere, L.; Buttes, N.; Feng, L.; Whitney, M.; Roemer, K.; Tsien, R.

Y. Science 1998, 2 79, 8488). As the only fluorogenic Bla substrate currently available, CCF2 has many successful applications in tissue culture (Zlokarnik, G.; Negulescu, P. A.; Knapp, T. E.; Mere, L.; Buttes, N.; Feng, L.; Whitney, M.; Roemer, K.; Tsien, R. Y. Science 1998, 2 79, 8488; Zlokarnik, G. *Methods in Enzymology* 2000, 326, 221-241; Whitney, M.; Rockenstein, E.; Cantin, G.; Knapp, T.; Zlokarnik, G.; Sanders, P.; Durick, K.; Craig, F. F.; negulescu, P. A. *Nat. Biotech.* 1998, 16, 1329-1333; Galarneau, A.; Primeau, M.; Trudeau, L.-E.; Michnick, S. W. *Nat. Biotech.* 2002, 20, 619-622; Wehrman, T.; Kleaveland, B.; Her, J.-H.; Balint, R. F.; Blau, H. M. *Proc. Natl. Acad. Sci. USA* 2002, 99, 3469-3474; Spotts, J. M.; Dolmetsch, R. E.; Greenberg, M. E. *Proc. Natl. Acad. Sci. USA* 2002, 99,15142-15147; Cavrois, M.; deNoronha, C.; Greene, W. C. *Nat. Biotech.* 2002, 20, 1151-1154), but its high molecular weight and low aqueous solubility have prevented applications in intact mammalian tissues or in cells with thick walls such as in yeast or plants.

One way to increase the sensitivity of a fluorescent reporter assay is to maximize the amount of a fluorescent signal generated by a single reporter enzyme. An optimal enzyme will convert $10^5$ substrate molecules per second under saturating conditions (see, Stryer, L. Introduction to Enzymes. In: Biochemistry, New York: W. H. Freeman and company, 1981, pp. 103-134). Beta-lactamases can cleave about $10^3$ molecules of a preferred substrates per second (see, Chang, Y. H. et al., Proc.Natl.Acad.Sci.USA 87: 2823-2827 (1990)). A preferred fluorescent product can produce up to $10^6$. In practice, a small fraction of the photons generated by the fluorescent product will be detected.

A good fluorescent substrate has a high turnover and optical properties such as high extinction and high fluorescence quantum yield. This present invention provides such fluorescent substrates and provides additional benefits as well.

SUMMARY

In one aspect, beta-lactamase substrate compounds are provided that are suitable for use in a reported gene assay. In another aspect, membrane-permeant compounds are provided which can be transformed into, or can be cleaved to release a portion that is, substantially membrane-impermeant. Such transformation or cleavage may typically occur after entry of the compound into a cell.

The novel beta-lactamase substrates disclosed herein are easily synthesized. Prior beta-lactamase substrates consist of a donor fluorophore and an acceptor chromophore connected by a cephalosporin. Fluorescence resonance energy transfer between the donor and acceptor is disrupted by beta-lactamase cleavage of the cephalosporin. The novel substrates disclosed herein comprise simpler phenolic ethers of cephalosporins in which beta-lactamase attack releases the free phenolic chromophore, which is then detectable by fluorescence, chemiluminescence, or formation of colored precipitates. One advantage over prior substrates is that the novel molecules are smaller, can more readily give long-wavelength absorbencies or fluorescence and give lower detection limits.

In one embodiment, compounds are provided that are substrates for beta-lactamase and that are suitable for use in a reporter gene assay. Such compounds may be, in some embodiments, membrane-permeant compounds that can be transformed into substantially membrane-impermeant compounds after entry into a cell.

In accordance with the present invention, compounds are provided having general formula 1:

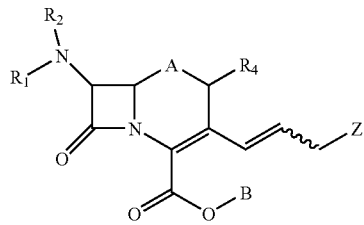

Formula 1 in which Z includes a fluorophore or chromophore and includes a group that may link to the lactam-containing group (such as, for example, a phenolic group, an amine, a thiophenol, thiol or thioether, or other group); $R_1$ and $R_2$ are independently selected from H, aliphatic, aromatic, alkyl, and acyl (including, for example, a benzyl, 2-thienylmethyl, or cyanomethyl group, or a quencher); $R_4$ is any substitution that does not compromise the efficiency of hydrolysis of the compound by beta-lactamase (including, for example, H and lower alkyl); B is selected from the group consisting of H, physiologically acceptable salts or metal, ester groups, ammonium cations, $—CHR_5OCO(CH_2)_nCH_3$, $—CHR_5OCOC(CH_3)_3$, acylthiomethyl, acyloxy-alpha-benz, deltabutyrolactonyl, methoxycarbonyloxymethyl, phenyl, methylsulphinylmethyl, beta-morpholinoethyl, dialkylaminoethyl, and dialkylaminocarbonyloxymethyl, in which $R_5$ is selected from the group consisting of H and lower alkyl; n is an integer between 0 and 10, inclusive, and is preferably an integer between 1 and 5, inclusive; and A is selected from the group consisting of S, O, SO, $SO_2$ and $CH_2$. In embodiments, the beta-lactam ring of the compounds disclosed herein may be cleaved by a beta-lactamase enzyme.

In another aspect, methods are provided for determining whether a beta-lactamase enzyme can cleave a compound of the present invention having the general formula 1, or a membrane permeant derivative thereof. The method involves contacting the sample with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates that the beta-lactamase enzyme can cleave the compound and that the compound is a substrate for the beta-lactamase enzyme.

In another aspect, methods are provided for determining whether a sample contains beta-lactamase activity. The method involves contacting the sample with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates the presence of beta-lactamase activity in the sample. One aspect of this method is for determining the amount of an enzyme in a sample by determining the degree of fluorescence emitted at a first and second time after contacting the sample with a compound of the present invention. The difference in the degree of fluorescence emitted from the sample at the first and second time is determined. That difference reflects the amount of a beta-lactamase enzyme in the sample.

In another aspect, the present invention is directed to screening assays using the compounds of the present invention and a host cell, such as a mammalian cell, transfected with at least one recombinant nucleic acid molecule encoding at least one protein having beta-lactamase activity. Such recombinant nucleic acid molecule comprise expression control sequences adapted for function in a eukaryotic cell, such as a vertebrate cell, operatively linked to a nucleotide sequence coding for the expression of a beta-lactamase enzyme. The present invention also provides recombinant nucleic acid molecules comprising expression control sequences adapted for function in a eukaryotic cell, such as a vertebrate cell, operably linked to a nucleotide sequence coding for the expression of a cytosolic beta-lactamase enzyme.

In another aspect, methods are provided for determining the amount of beta-lactamase activity in a cell. This method involves providing a sample comprising a host cell transfected with a recombinant nucleic acid molecule comprising a host cell having expression control sequences operatively linked to nucleic acid sequences coding for the expression of a beta-lactamase enzyme. The sample can comprise whole host cells, or an extract of the host cells, which is contacted with a compound of the present invention. The amount of compound cleaved is measured, whereby the amount of substrate cleaved is related to the amount of beta-lactamase activity in the host cell.

In another aspect, methods are provided for monitoring the expression of a gene operably linked to a set of expression control sequences. The methods involve providing a host eukaryotic cell transfected with a recombinant nucleic acid molecule. The nucleic acid molecule comprises a set of expression control sequences operatively linked to nucleic acid sequences coding for the expression of a beta-lactamase enzyme, except if the host eukaryotic cell is a fungus, the beta-lactamase is a cytosolic beta-lactamase enzyme. A sample comprising the host eukaryotic cell, or an extract or conditioned medium produced therefrom or thereby, with a compound of the present invention. The amount of compound cleaved is determined using the methods of the present invention, wherein the amount of substrate cleaved is related to the amount of beta-lactamase activity in the host eukaryotic cell, which is related to the expression of the gene.

In another aspect, methods are provided for determining whether a test compound alters the expression of a gene operably linked to a set of expression control sequences. The methods involve providing a host eukaryotic cell transfected with a recombinant nucleic acid construct. The recombinant nucleic acid construct comprises a set of expression control sequences operably linked to nucleic acid sequences coding for the expression of a beta-lactamase enzyme except if the host eukaryotic cell is a fungus, wherein the beta-lactamase is a cytosolic beta-lactamase enzyme. The host eukaryotic cell is contacted with the test compound. This host eukaryotic cell is then contacted with a compound of the present invention. The amount of the compound of the present invention cleaved is then measured using the methods of the present invention, whereby the amount of the compound of the present invention cleaved is related to the amount of beta-lactamase activity in the cell.

In another aspect, methods are provided for clonal selection by providing cells transfected with a recombinant nucleic acid molecule comprising at least one expression control sequences operably linked to at least one nucleic acid sequence coding for the expression of a cytosolic beta-lactamase enzyme. The cells are contacted with a substance that activates, inhibits, or has no effect on the activation of the expression control sequence. The cells are contacted with a compound of the present invention. The amount of the compound of the present invention cleaved is determined within individual cells (including each individual cell), whereby the amount of the compound of the present invention cleaved reflects the amount of beta-lactamase activity in the cells. Cells having a selected level of beta-lactamase activity are selected and propagated.

Another aspect of the present invention includes the use of a beta-lactamase reporter gene and a compound of the present invention to screen test chemicals for biochemical activity within at least one cell comprising providing cells transfected with a recombinant nucleic acid molecule. The recombinant nucleic acid molecule comprises at least one expression control sequence operably linked to at least one nucleic acid sequence encoding for the expression of a beta-lactamase enzyme. The cells are contacted with a test chemical that may activate, inhibit, or have no effect on the activation of the expression control sequence. The cells are contacted with a compound of the present invention and the amount of the compound cleaved is measured. The amount of compound cleaved reflects the amount of beta-lactamase activity within the at least one cell, which reflects a biochemical activity within the at least one cell.

DETAILED DESCRIPTION

Definitions

Figure 1:
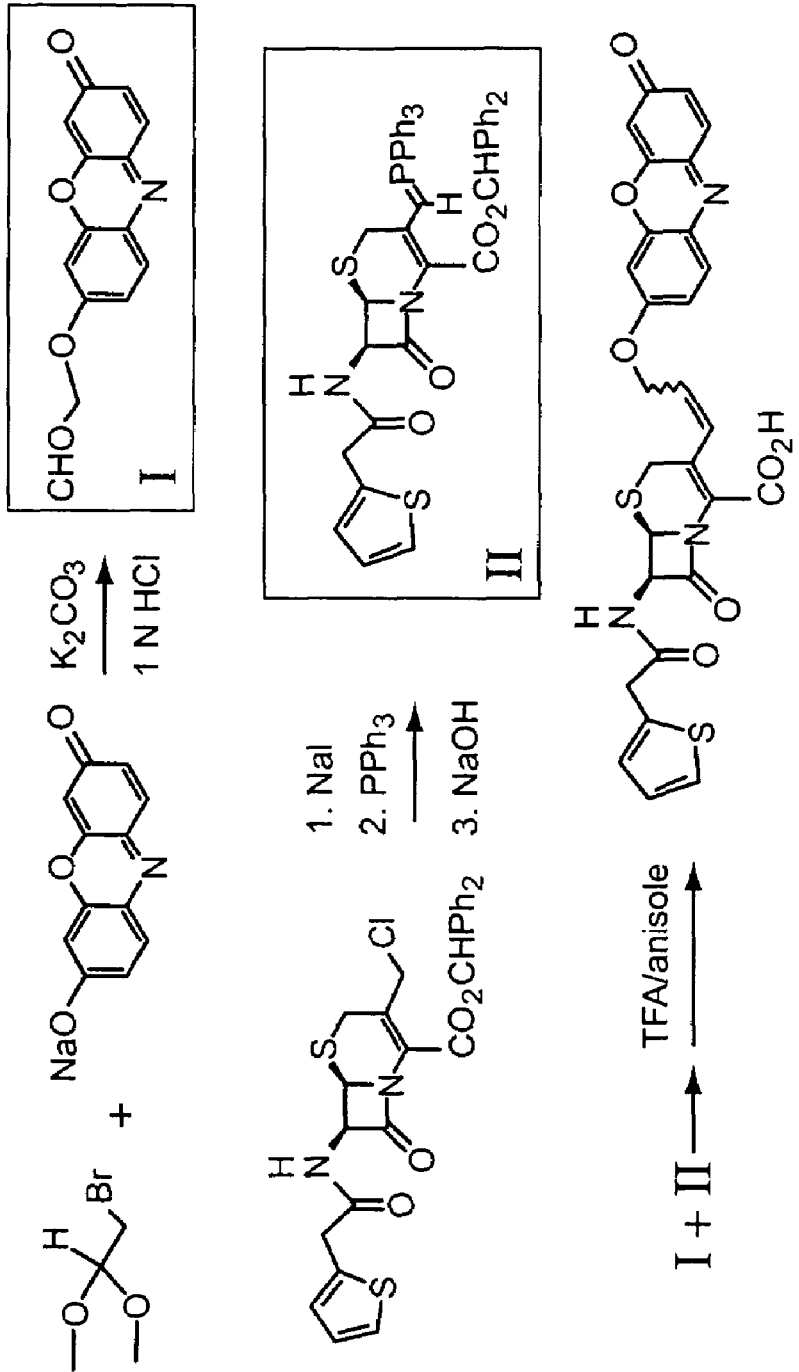
FIG. 1 shows the new substrate is synthetically easily accessible.

In accordance with the present invention and as used herein, the following terms are defined with the following meanings, unless stated otherwise.

The term "alkyl" refers to straight, branched, and cyclic aliphatic groups of 1 to 8 carbon atoms, preferably 1 to 6 carbon atoms, and most preferably 1 to 4 carbon atoms. The term "lower alkyl" refers to straight and branched chain alkyl groups of 1 to 4 carbon atoms.

The term "acyl" refers to —C(O)R', in which R' is a straight, branched, or cyclic aliphatic group of 1 to 8 carbon atoms, preferably 1 to 6 carbon atoms, and most preferably 1 to 4 carbon atoms.

The term "aliphatic" refers to saturated and unsaturated alkyl groups of 1 to 10 carbon atoms, preferably 1 to 6 carbon atoms, and most preferably 1 to 4. carbon atoms.

The term "derivative" means a derivative of a compound that retains the underlying chemical structural of the original compound, or if the underlying structure has changed, can be readily converted into the original compound.

The term "beta-lactamase enzyme" refers to an enzyme that can cleave a beta-lactam ring. Examples of a beta-lactamase enzyme include the naturally occurring forms of beta-lactamase and enzymes that have been prepared by mutagenesis of beta-lactamase enzymes. If a beta-lactamase enzyme can cleave the beta-lactam ring in particular compound having the general formula 1 (or its membrane permeant derivative), then this particular compound is a substrate of this invention for this particular beta-lactamase enzyme (see, for example, WO 96/30540, published Oct. 3, 1996).

The term "membrane-permeant derivative" means a chemical derivative of a compound of general formula 1, wherein any primary amine has been acylated or any carboxyl or —SO$_3$H moiety has been esterified. These derivatives are better able to cross cell membranes, i.e., membrane permeant, because hydrophilic groups are masked to provide more hydrophobic derivatives. For example, some embodiments of a "membrane-permeant derivative" are chemical derivatives of a compound of general formula 1 containing at least one acylated aromatic hydroxyl, acylated amine, or alkylated aromatic hydroxyl wherein the acyl group contains 1 to 5 carbon atoms and wherein the alkyl group is selected from the group consisting of —CH$_2$OC(O)alk, —CH$_2$SC(O)alk, —CH$_2$OC(O)Oalk, lower acyloxy-alpha-benzyl, and deltabutyrolactonyl; wherein alk is lower alkyl of 1 to 4 carbon atoms. Such derivatives are better able to cross cell membranes than other compounds, and so may be termed "membrane permeant," because hydrophilic groups are masked to provide more hydrophobic derivatives. Also, the masking groups are designed to be cleaved from the fluorogenic substrate within the cell to generate the derived substrate intracellularly. Because the substrate, after cleavage, is more hydrophilic than the membrane permeant derivative it is now trapped within the cells.

The term "dye" refers to a molecule or part of a compound that absorbs specific frequencies of light, including but not limited to ultraviolet light. Dyes include phenolic dyes, such as, for example, umbelliferone, fluorescein, and resorufin; aromatic amines, and other compounds, such as, for example, rhodamine. The terms "dye" and "chromophore" are synonymous.

The term "fluorophore" refers to a chromophore that fluoresces.

The term "fluorophore precursor" refers to a molecule that has a chromophore that fluoresces following cleavage to release a fluorophore-containing moieity.

The term "fluorescent donor moiety" refers the radical of a fluorogenic compound which can absorb energy and is capable of transferring the energy to another fluorogenic molecule or part of a compound. Suitable donor fluorogenic molecules include, but are not limited to, coumarins and related dyes; xanthene dyes such as fluoresceins, rhodols, and rhodamines; resorufins; cyanine dyes; bimanes; acridines; isoindoles; dansyl dyes; aminophthalic hydrazides such as luminol and isoluminol derivatives; aminophthalimides; aminonaphthalimides; aminobenzofurans; aminoquinolines; dicyanohydroquinones; and europium and terbium complexes and related compounds. Accordingly, a donor fluorescent moiety can be a dye or chromophore.

The term "quencher" refers to a chromophoric molecule or part of a compound which is capable of reducing the emission from a fluorescent donor when attached to the donor. Quenching may occur by any of several mechanisms including, for example, quenching of a single fluorophore or chromophore in a molecule of general formula 1, fluorescence resonance energy transfer between fluorophores and/or chromophores, photoinduced electron transfer, paramagnetic enhancement of intersystem crossing, Dexter exchange coupling, and exciton coupling such as the formation of dark complexes. For example, in a vinylogous cephalosporin, a flurophore linked via a linker containing a vinyl linkage to the cephalosporin may be quenched, and may regain fluorescence upon cleavage of the linker.

The term "acceptor" as used herein refers to a quencher which operates via fluorescence resonance energy transfer. Many acceptors can reemit the transferred energy as fluorescence. Examples of moieties that may serve as quencher or acceptor include coumarins and related fluorophores, xanthenes such as fluoresceins, rhodols and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

Beta-Lactamases are excellent enzymes due to their diffusion-controlled catalysis of beta-lactam hydrolysis (Christensen, H. et al., Biochem. J. 266:853-861 (1990)). Upon examination of the other properties of this class of enzymes, it was determined that they were suited to the task of an intracellular reporter enzyme. They cleave the beta-lactam ring of beta-lactam antibiotics, such as penicillins and cephalosporins, generating new charged moieties in the process (O'Callaghan, C. H. et al., Antimicrob. Agents. Chemother. 8:57-63, (1968); Stratton, C. W., J. Antimicrob. Chemother. 22, Suppl. A: 23-35 (1988)). A first generation cephalosporin is illustrated below, 1, with the arrow pointing to the site of cleavage by beta-lactamase. The group $R_1$ of cephalosporin 1 may be any group suitable as part of a cephalosporin. The free amino group thus generated 2 donates electron density through the vinyl group to promote irreversible cleavage of a nucleofugal group $R_2$ from the 3'-position. $R_2$ is thus free to diffuse away from the $R_1$-cephalosporin conjugate 3. (Please note that the terms $R_1$ and $R_2$ in the scheme below are not to be taken as being limited to the definitions of those terms as used in other examples either supra or infra.)

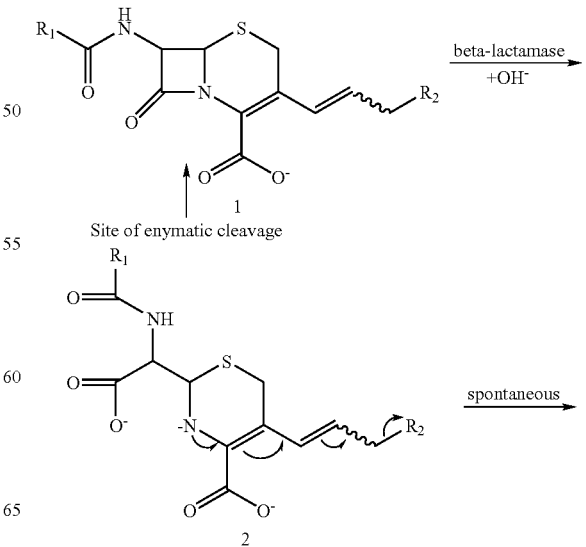

-continued

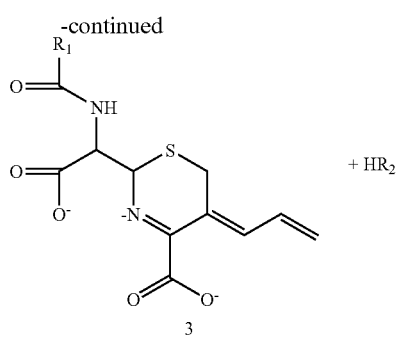

Beta-Lactamases are a class of enzymes that have been very well characterized due to their clinical relevance in making bacteria resistant to beta-lactam antibiotics (Waley, S. G., Sci. Prog. 72:579-597 (1988); Richmond, M. H. et al., Ann. N.Y. Acad. Sci. 182:243-257 (1971)). Most beta-lactamases have been cloned and their amino acid sequence determined (see, e.g., Ambler, R. P., Phil. Trans. R. Soc. Lond. Ser. B. 289:321-331 (1980)).

A gene encoding beta-lactamase is known to molecular biologists as the ampicillin resistance gene (Amp.sup.r) and is commonly used to select for successfully transduced bacteria (Castagnoli, L. et al., Genet.Res. 40: 217-231 (1982)); clones thereof are almost universally available. The enzyme catalyzes the hydrolysis of a beta-lactam ring and will not accept peptides or protein substrates (Pratt, R. F. and Govardhan, C. P., Proc. Natl. Acad. Sci. USA 81:1302-1306 (1984); Murphy, B. P. and Pratt, R. F., Biochemistry 30:3640-3649 (1991)). The kinetics of this reaction is well understood and there is no product inhibition (Bush, K. and Sykes, R. B., Antimicrob. Agents. Chemother. 30:6-10 (1986); Christensen et al. (1990), supra). The enzyme substrates are less polar than the products.

The carboxyl group in the substrate can be easily masked by an acetoxymethyl ester (Jansen, A. B. A. and Russell, T. J., J. Chem. Soc. 2127-2132, (1965); Daehne, W. et al., J. Med. Chem. 13:607-612 (1970)), which is readily cleaved by endogenous mammalian intracellular esterases. Conversion by these esterases followed by cleavage of the beta-lactam by beta-lactamase generates two negative charges and a tertiary amine. Multiple chromogenic substrates of different design have been reported and are commercially available (Jones, R. N. et al., J. Clin. Microbiol. 15:677-683 (1982); Jones, R. N. et al., J. Clin. Microbiol. 15:954-958 (1982); O° Callaghan, C. H. et al., Antimicrob. Agents. Chemother. 1:283-288 (1972)).

A large number of beta-lactamases have been isolated and characterized, all of which would be suitable for use in accordance with the present invention. Initially, beta-lactamases were divided into different classes (I through V) on the basis of their substrate and inhibitor profiles and their molecular weight (Richmond, M. H. and Sykes, R. B., Adv. Microb. Physiol. 9:31-88 (1973)). More recently, a classification system based on amino acid and nucleotide sequence has been introduced (Ambler, R. P., Phil. Trans. R. Soc. Lond. Ser. B. 289:321-331 (1980)). Class A beta-lactamases possess a serine in the active site and have an approximate weight of 29 kd. This class contains the plasmid-mediated TEM beta-lactamases such as the RTEM enzyme of pBR322. Class B beta-lactamases have an active-site zinc bound to a cysteine residue. Class C enzymes have an active site serine and a molecular weight of approximately 39 kd, but have no amino acid homology to the class A enzymes.

The coding region of an exemplary beta-lactamase which may be employed in the present invention is described in U.S. Pat. No. 5,955,604. The pTG2dell containing this sequence has been described (Kadonaga, J. T. et al., J. Biol. Chem. 259:2149-2154 (1984)). The entire coding sequence of wild-type pBR322 beta-lactamase has also been published (Sutcliffe, J. G., Proc. Natl. Acad. Sci. USA 75:3737-3741 (1978)). As would be readily apparent to those skilled in the field, this and other comparable sequences for peptides having beta-lactamase activity would be equally suitable for use in accordance with the present invention. The beta-lactamase reporter gene is employed in an assay system in a manner well known per se for the use of reporter genes (for example, in the form of a suitable plasmid vector).

In conjunction with a suitable beta-lactamase, there are employed, in accordance with the present methods and compositions, fluorogenic substrates of the general formula 1:

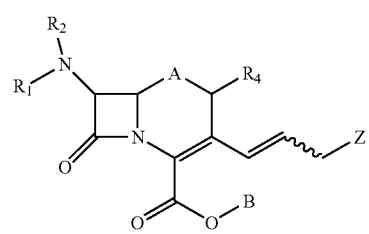

Formula 1 in which Z includes a fluorophore or chromophore and includes a group that may link to the lactam-containing group (such as, for example, a phenolic group, an amine, a thiophenol, thiol or thioether, or other group); $R_1$ and $R_2$ are independently selected from H, aliphatic, aromatic, alkyl, and acyl (including, for example, a benzyl, 2-thienylmethyl, or cyanomethyl group, or a quencher); $R_4$ is any substitution that does not compromise the efficiency of hydrolysis of the compound by beta-lactamase (including, for example, H and lower alkyl); B is selected from the group consisting of H, physiologically acceptable salts or metal, ester groups, ammonium cations, $-CHR_5OCO(CH_2)_nCH_3$, $-CHR_5OCOC(CH_3)_3$, acylthiomethyl, acyloxy-alpha-benz, deltabutyrolactonyl, methoxycarbonyloxymethyl, phenyl, methylsulphinylmethyl, beta-morpholinoethyl, dialkylaminoethyl, and dialkylaminocarbonyloxymethyl, in which $R_5$ is selected from the group consisting of H and lower alkyl; n is an integer between 0 and 10, inclusive, and is preferably an integer between 1 and 5; and A is selected from the group consisting of S, O, SO, $SO_2$ and $CH_2$. In embodiments of the compounds disclosed herein, the beta-lactam ring may be cleaved by a beta-lactamase enzyme.

For example, in Formula 1 above $R_2$ may be H and $R_1$ may be an acyl group with a substituent R' linked to the carbonyl carbon, in which R' is a benzyl, 2-thienylmethyl, or cyanomethyl group. Z includes a fluorescent moiety. In embodiments, the Z may be selected from the group consisting of:

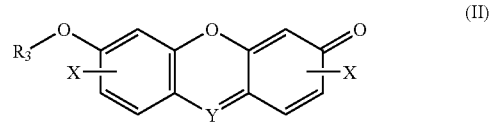

(II)

R₃ is a linker for the fluorescent moiety. The linker R₃ serves the purpose of attaching the fluorescent moiety to the cephalosporin phenol ether derived backbone. Suitable linkers for use as R₃ include, but are not limited to, a direct bond to a heteroatom (e.g., O, N or S) in the dye's chromophore or the following: $-O(CH_2)_n-$, $-S(CH_2)_n-$, $-NR_5(CH_2)_n-$, $-N^+R_5(CH_2)_n$, $-OCONR_5(CH_2)_n-$, $-O_2C(CH_2)_n-$, $-SCSNR_5(CH_2)_n$, $-SCSO(CH_2)_n-$, $-S(CH_2)_nCONR_5(CH_2)_m$, $-S(CH_2)_nNR_5CO(CH_2)_m$, and in which R₅ is selected from the group of H and lower alkyl, n is an integer between 0 and 10, inclusive, and is preferably an integer between 1 and 5, inclusive; and m is an integer from 0 to 4, inclusive. Particularly preferred groups are $-S(CH_2)_n$. Also preferred is H. In a one aspect, the compounds are membrane-permeant.

Beta-lactamases cleave the beta-lactam ring of beta-lactam antibiotics, such as penicillins and cephalosporins, generating new charged moieties in the process (see, O'Callaghan, C. H. et al., Antimicrob.Agents.Chemother. 8: 57-63, (1968); and Stratton, C. W., J. Antimicrob. Chemother. 22, Suppl. A: 23-35 (1988)). For example, cleavage of a 1-aryl-beta-lactam compound by beta-lactamase produces a propionic acid functionality attached to the aryl amine, and at physiological pH, this cleaved compound has an additional negative charge because of the acid functionality.

The starting material, product, and product after being cleaved by a beta-lactamase can be non-fluorescent, short-wavelength fluorescent (meaning, for this purpose, that the excitation and/or emission wavelengths of the product are shorter than those of the starting material) or long-wavelength fluorescent (meaning, for this purpose, that the excitation and/or emission wavelengths of the product are equal to or longer than those of the starting material). Compounds of general formula 1 (and their membrane permeant derivatives) will have different fluorescent properties from their fluorophore precursor. Formation of the beta-lactam ring will shift the fluorescence of the fluorophore precursor to shorter wavelength or even abolishes their fluorescence. Cleavage of the beta-lactam will essentially restore the fluorescence of the fluorophore precursor (with some possible differences that are attributable to the propionic acid moiety that is attached to what was previously a primary amine in the fluorophore precursor). Thus compounds of general formula 1 may be used as enzyme assay indicators, indicating, for example, the activity of beta-lactamase by increased or altered fluorescence following cleavage by beta-lactamase. Such compounds are useful and effective to indicate beta-lactamase activity when comprising only a single flurophore or chromophore.

A class of compounds useful in the practice of the invention includes β-lactam compounds where a phenolate is linked to a vinylogous cephalosporin, effective that cleavage of the β-lactam ring by β-lactamase releases a phenolate from the vinylogous cephalosporin. Cleavage of the β-lactam ring of a cephalosporin creates a free amino group, which triggers spontaneous elimination of any leaving group previously attached to the 3' position. A suitable leaving group may be, for example, umbelliferone.

In other embodiments, compounds of general formula 1 may comprise two, or may comprise more than two, fluorophores or chromophores. As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large. extinction coefficient at wavelengths coinciding with the emission of the donor. The dependence of fluorescence energy transfer on the above parameters has been reported (Forster, T. (1948) Ann. Physik 2:55-75; Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, Vol 30, ed. Taylor, D. L. & Wang, Y.-L., San Diego: Academic Press (1989), pp. 219-243; Turro, N. J., Modem Molecular Photochemistry, Menlo Part: Benjamin/Cummings Publishing Co., Inc. (1978), pp. 296-361), and tables of spectral overlap integrals are readily available to those working in the field (for example, Berlman, I. B. Energy transfer parameters of aromatic compounds, Academic Press, New York and London (1973)). The distance between donor fluorophore and acceptor dye at which fluorescence resonance energy transfer (FRET) occurs with 50% efficiency is termed $R_0$ and can be calculated from the spectral overlap integrals. For the donor-acceptor pair fluorescein tetramethyl rhodamine which is frequently used for distance measurement in proteins, this distance $R_0$ is around 50-70 Å (dos Remedios, C. G. et al. (1987) J. Muscle Research and Cell Motility 8:97-117). The distance at which the energy transfer in this pair exceeds 90% is about 45Å. When attached to the cephalosporin backbone the distances between donors and acceptors are in the range of 10 Å to 20 Å, depending on the linkers used and the size of the chromophores. For a distance of 20A, a chromophore pair will have to have a calculated $R_0$ of larger than 30 Å for 90% of the donors to transfer their energy to the acceptor, resulting. in better than 90% quenching of the donor fluorescence. Cleavage of such a cephalosporin by beta-lactamase relieves quenching and produces an increase in donor fluorescence efficiency in excess of tenfold. Accordingly, it is apparent that identification of appropriate donor-acceptor pairs for use as taught herein in accordance with the present invention would be essentially routine to one skilled in the art.

To measure beta-lactamase activity in the cytoplasm of living cells, smaller molecular weight chromophores as hereinafter described are in general preferred over larger ones as substrate delivery becomes a problem for larger compounds. Large molecules, especially those over about 1200 daltons, also tend to bind more avidly to cellular constituents than small ones, thereby removing at least some of them from access and cleavage by beta-lactamase.

Examples of suitable fluorophores and chromaphores are disclosed in U.S. Pat. Nos. 5,741,657 and 5,955,604, the disclosures of which are incorporated herein by reference in its entirety.

There are a number of synthetic routes for the formation of beta-lactam ring systems (see, Heusler, In: Cephalosporins and Penicillins: Chemistry and Biology, ed Flynn, Academic Press, New York., pp. 255-280 (1972); Sammes, Chem. Reviews 76:113-155 (1976); Cooper, In topics in Antibiotic Chemistry. Vol. 3, ed. Sammes et al., Ellis Horwood, Ltd, Chichester, U. K., pp. 39-199 (1980); Jung et al., Topics in Antibiotic Chemistry, Vol. 4, Ellis Horwood, Ltd. Chichester, U. K., pp. 11-241 (1980); Ernest, In: Chemistry and biology of Beta-Lactam Antibiotics, Vol. 2. Nontraditional Beta-Lactam Antibiotics, ed Morin et al., Academic Press, New York., pp. 315-361 (1982); Holden, In: Chemistry and Biology of Beta-Lactam Antibiotics, Vol. 2. Notraditional Beta-Lactam Antibiotics, ed. Morin et al., Academic Press, pp. 101-165 (1982); Koster et al., In: Chemistry and Biology of Beta-Lactam Antibiotics, Vol. 3., the Biology of Beta-Lactam Antibiotics, ed. Morin et al., Academic Press, New York., pp. 339-378 (1982); Christensen and Salzmann, In. Handbok of Experimental Pharmacology. Vol. 67/I. Antiobiotics Containing the Beta-Lactam Structure, ed. Demain et al., Springer-Verlag, Berlin, pp. 329-354 (1983); Durckheimer et al. In. Fontiers of Antibiotic Research, ed. Umezawa, Academic Press, Tokyo, pp. 161-192 (1987)).

The chemistry of the formation of 3-amino-2-azetidinones has been reviewed recently (see, Van der Steen and Van Koten, 1992). Beta-lactams of a series of substituted anilines have been prepared, and some of them were found to be competitive inhibitors, but not substrates, of several different types of beta-lactamase enzyme (see, Zrihen et al. Eur. J. Med. Chem. Chim. Ther. 18:307-314(1983); and Joyeau et al. J. Med. Chem. 31:370-374 (1988)).

A general method for synthesis of compounds of general formula 1 is depicted below (Scheme 1). As one of ordinary skill in the art will appreciate, the methods below can be used for a variety of derivatives, and other methods of synthesis are possible.

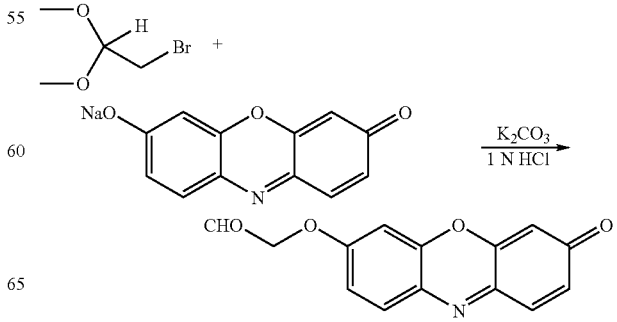

Scheme 1

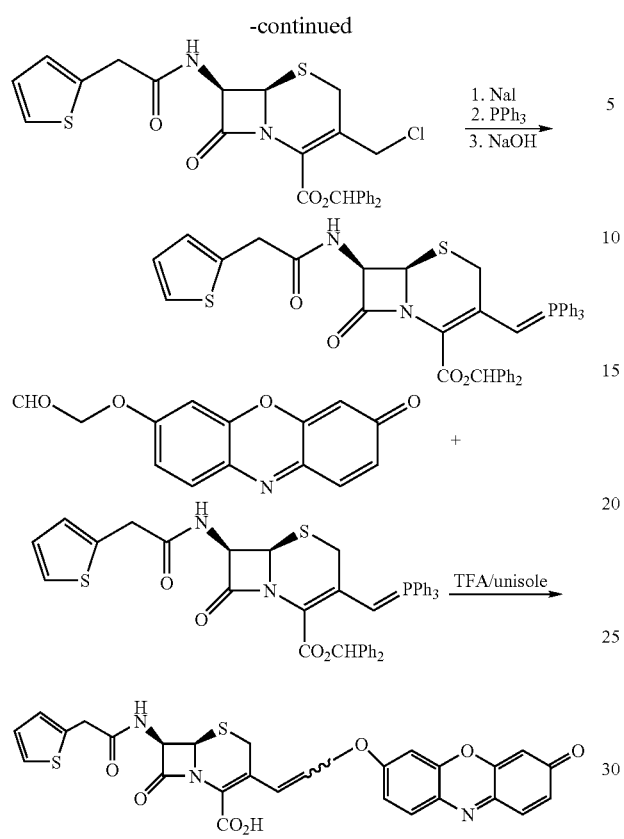

Figure 2:
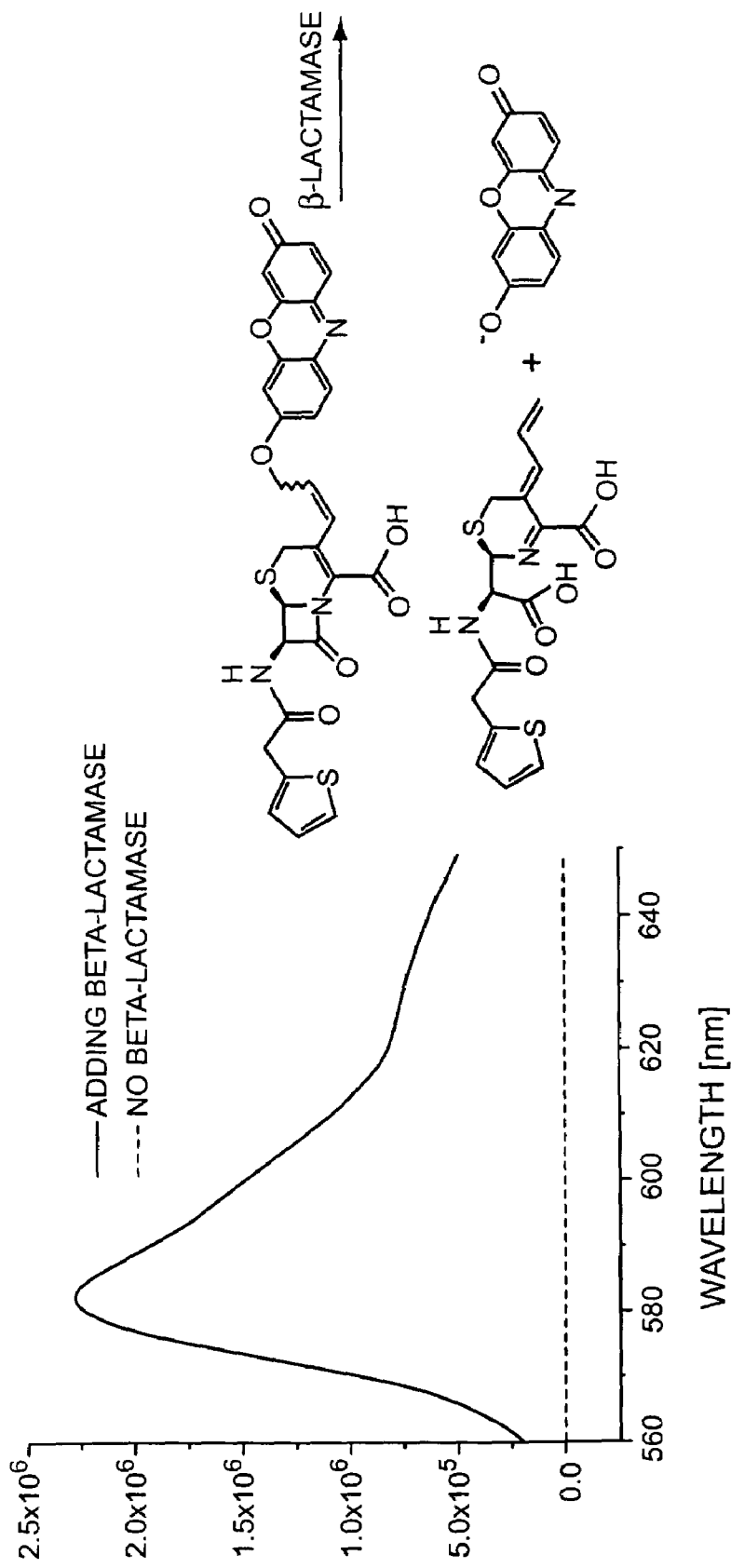
FIG. 2 shows enzymatic fragmentation can take place to the new substrate.
Figure 3:
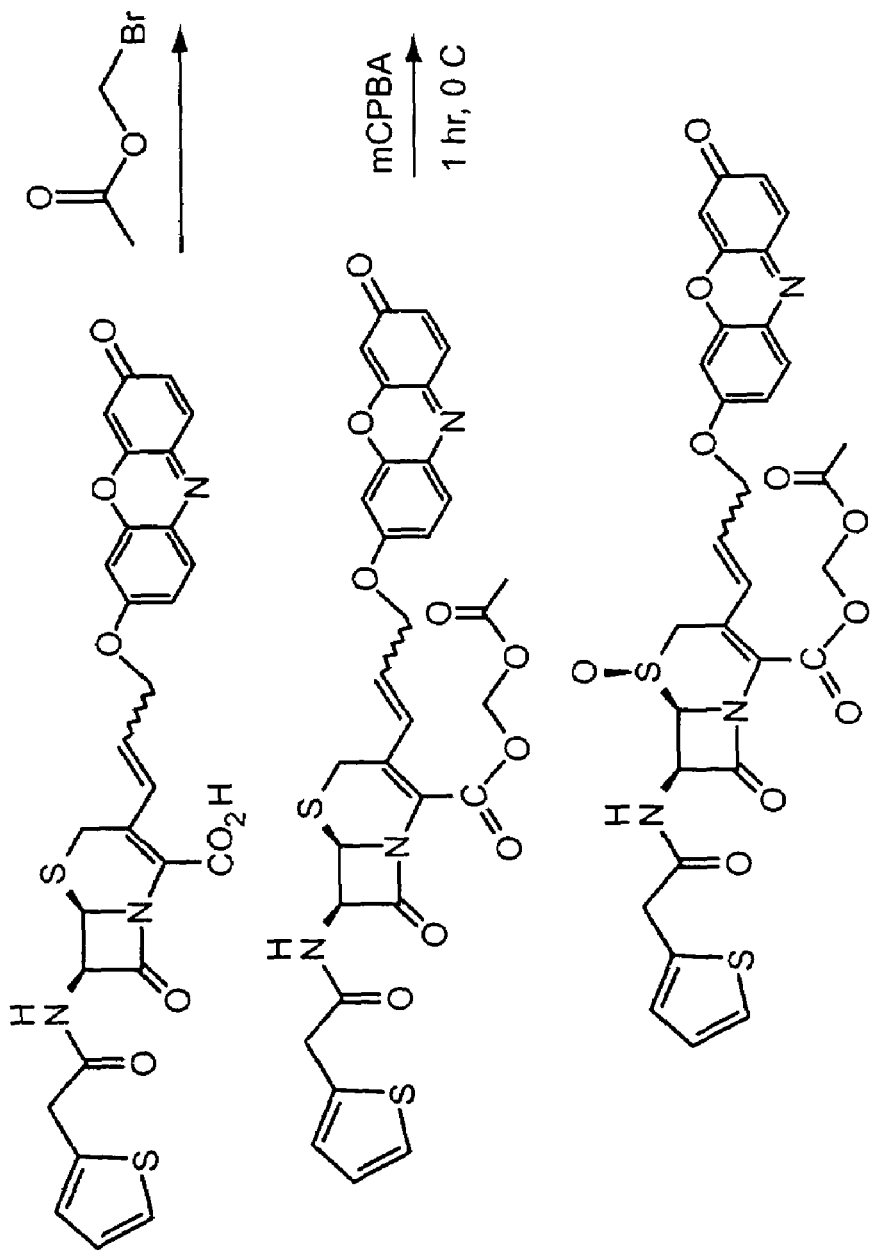
FIG. 3 shows synthesis of RECTO.
Figure 4:
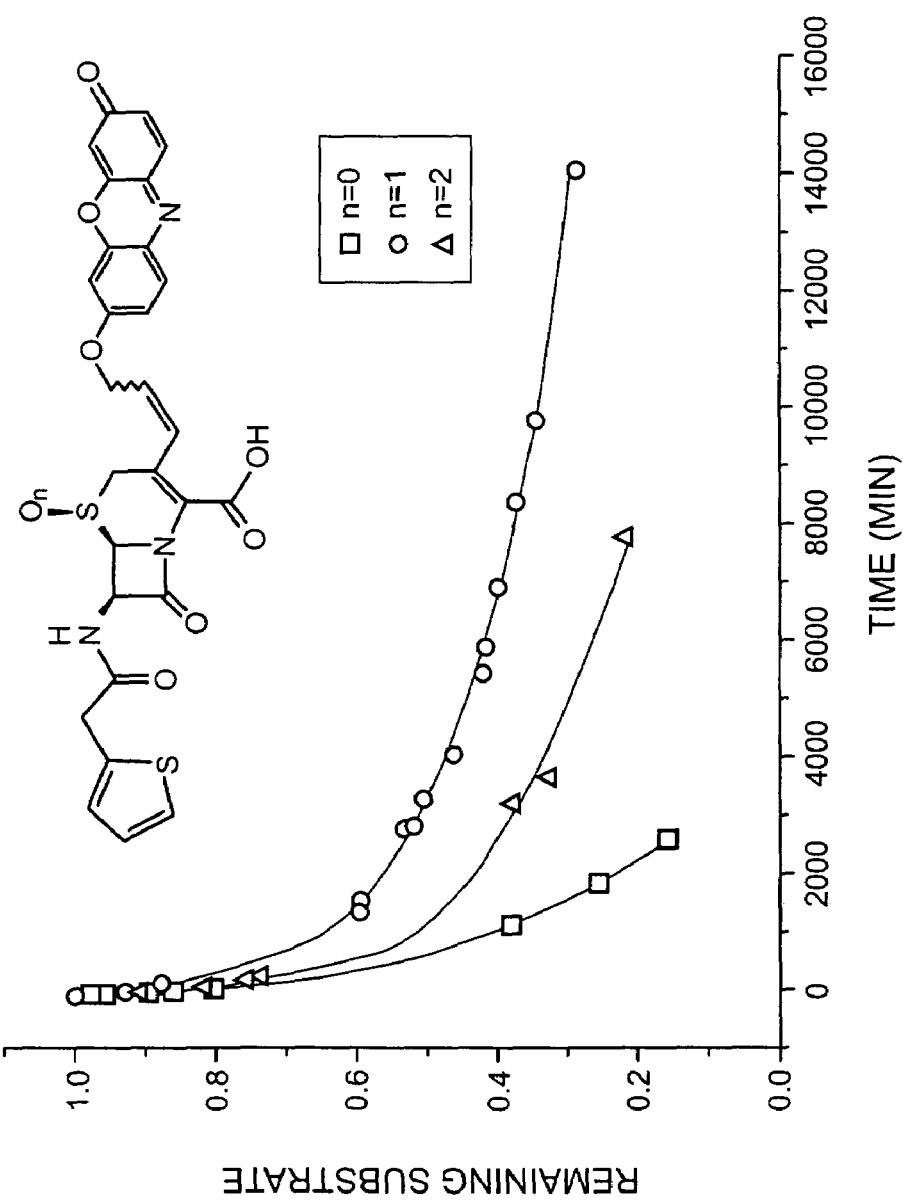
FIG. 4 shows oxidation state of the sulfide affects stability of the substrate.
Figure 5:
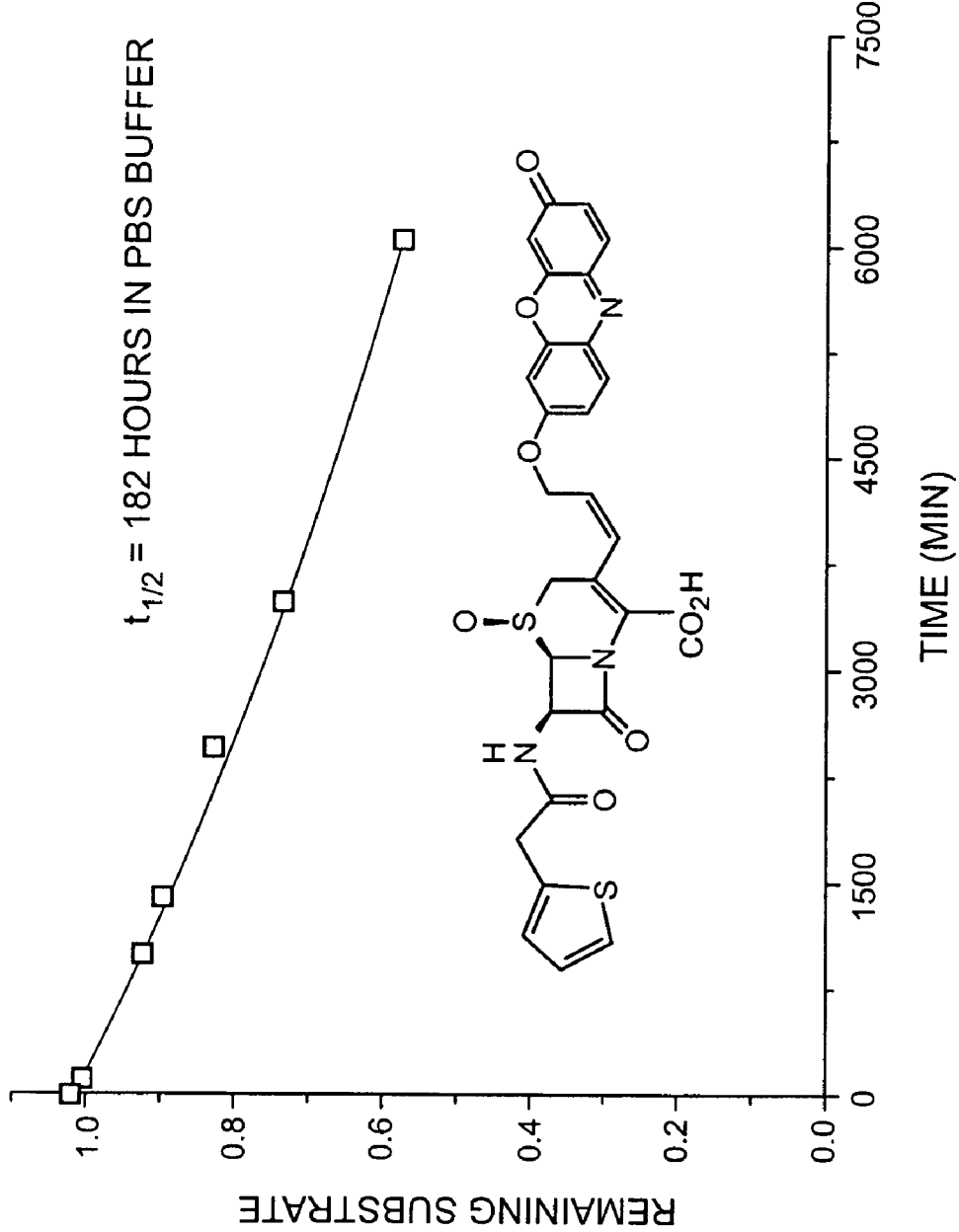
FIG. 5 shows sulfoxide increases substrate stability.
Figure 6:
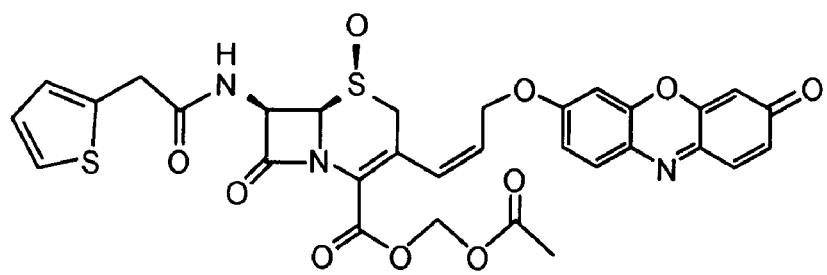
FIG. 6 shows increased resorufin deposition in beta-lactamase-transfected vs. wild type cells.
Figure 6:
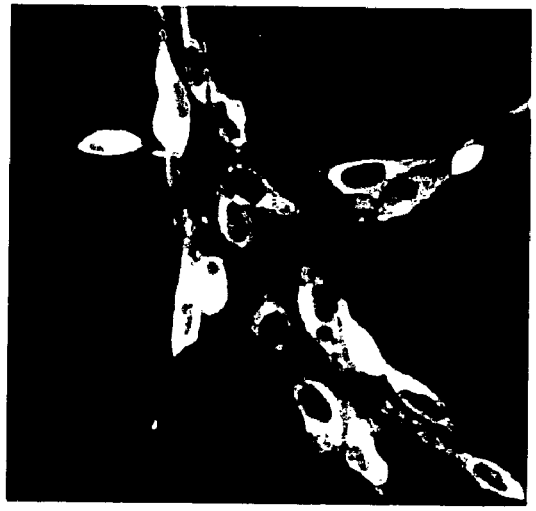
Figure 6:
Figure 7:
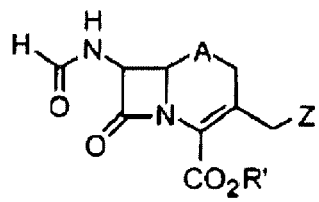
FIG. 7 shows cephalosporin-phenol.
Figure 7:
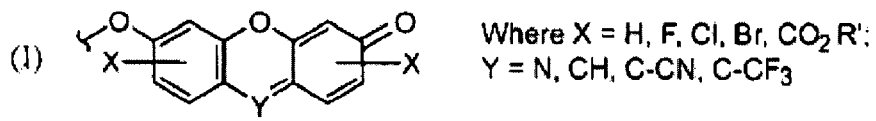
Figure 7:
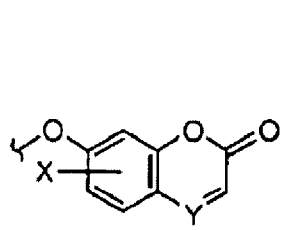
Figure 8:
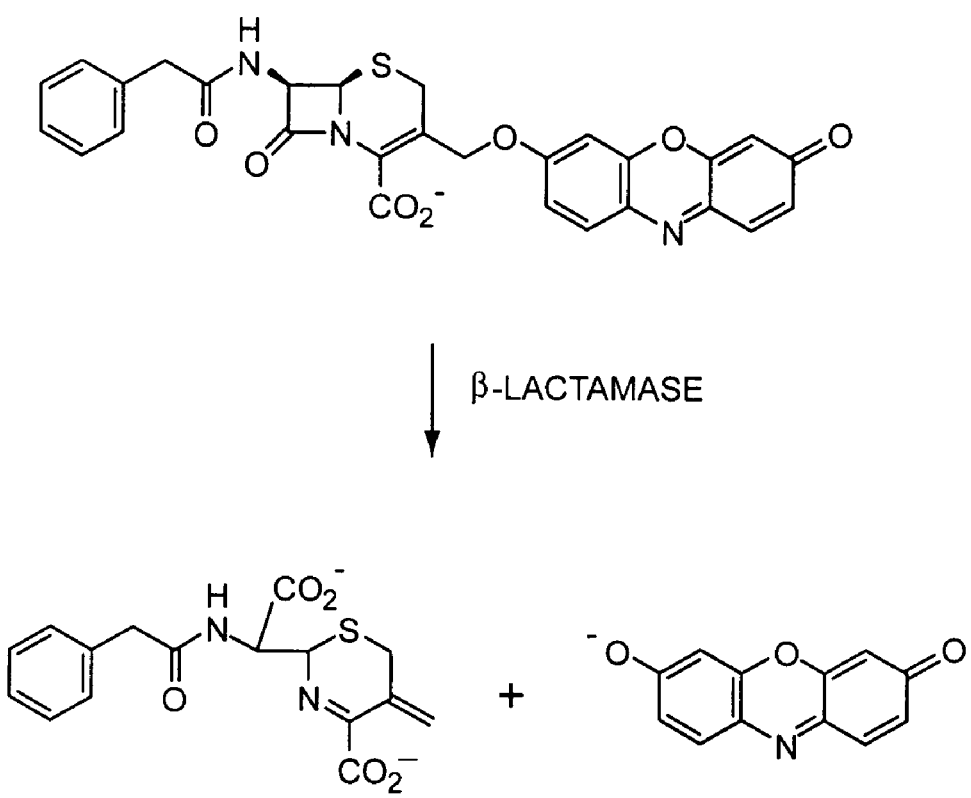
FIG. 8 shows resorufin-cephalosporin cleaved by beta-lactamase.
Figure 9:
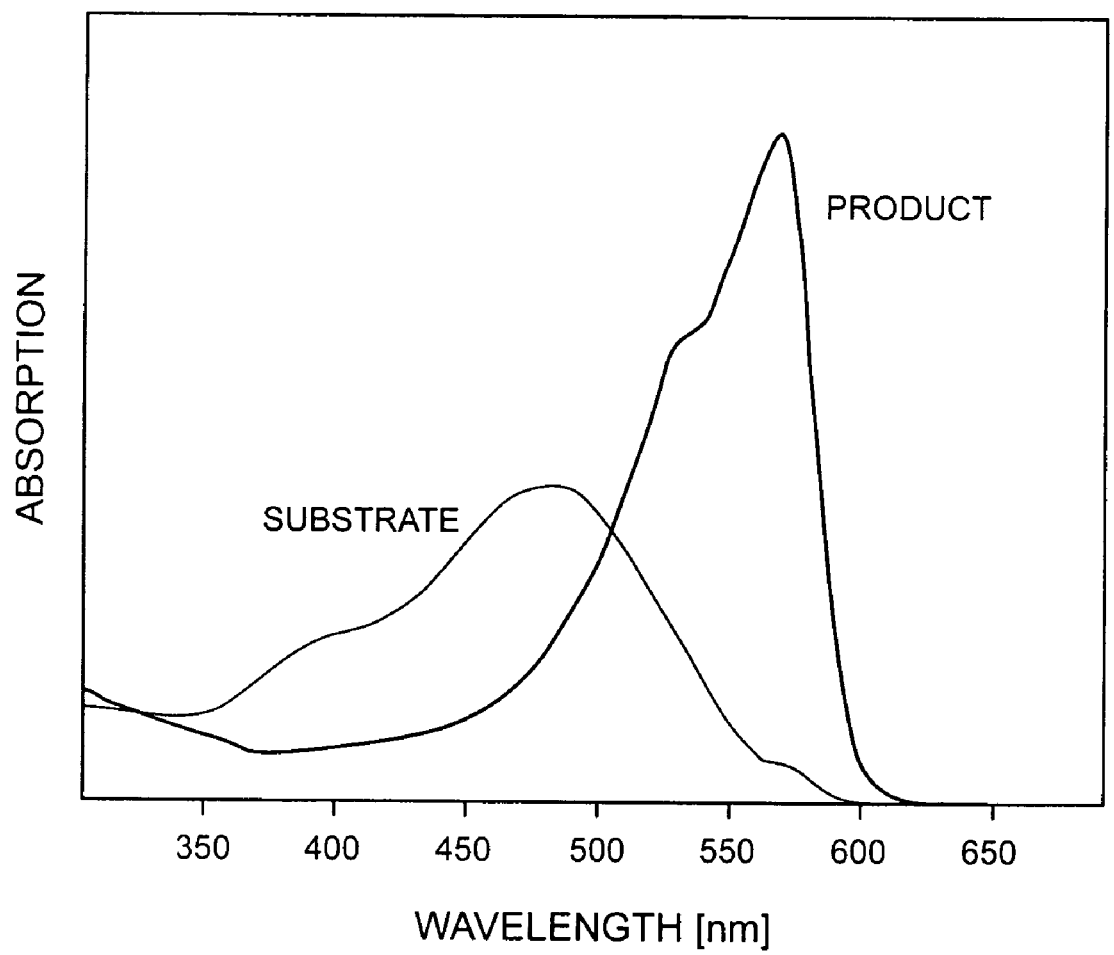
FIG. 9 shows absorption spectra of resorufin-cephalosporin before and after beta-lactamase treatment.
Figure 10:
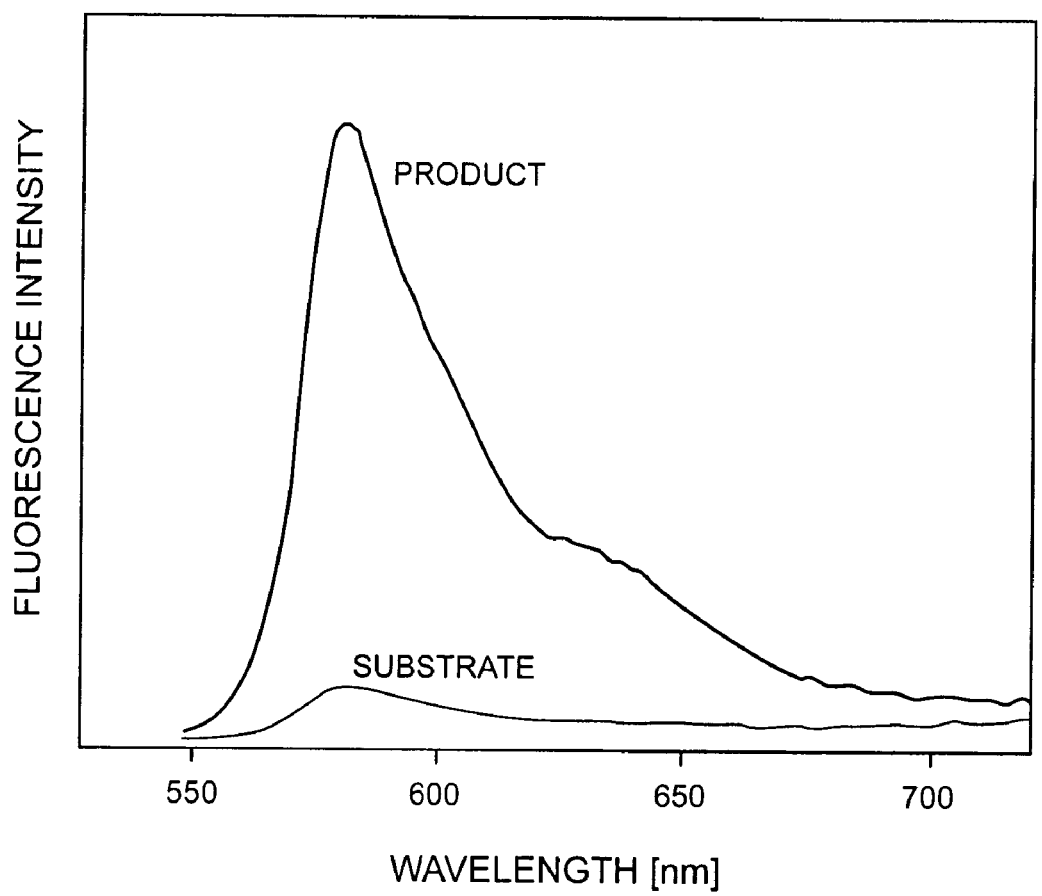
FIG. 10 shows fluorescence emission of resorufin-cephalosporin before and after beta-lactamase treatment.

The synthetic scheme depicted above is also illustrated in FIG. 1. The effect of cleavage of such a compound by beta-lactamase is illustrated in FIG. 2, where the upper curve indicating fluorescence is found in the presence of beta-lactamase enzyme, while the lower curve, indicating lack of significant fluorescence intensity, is found in the absence of beta-lactamase enzyme. A scheme for the synthesis of the compound CR2/AM (termed "RECTO" in the figure) is illustrated in FIG. 3. The oxidation of the sulfide linked to the lactam effects the stability of the compounds disclosed herein, as is illustrated in FIG. 4 and FIG. 5. The fluorescence of compounds disclosed herein is increased in cells containing higher levels of beta-lactamase enzymes, as illustrated in FIG. 6. A scheme illustrating the action of beta-lacatamase enzyme is illustrated in FIG. 8, and the effects of beta-lactamase action on a cephalosporin compound having features disclosed herein are shown in FIG. 9 and FIG. 10. Examples of compounds are shown in FIG. 7.

Table 1 depicts other cephempropenyl phenol ethers synthesized, where the terms R, A, R', and Z are as indicated in general formula 2:

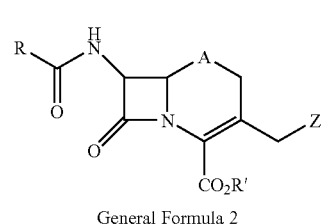

General Formula 2

TABLE 1

| Compound | R | A | R' | cis/trans | Z |
|---|---|---|---|---|---|
| 1 | CH$_3$ | S | H | mix | ![structure] |
| 2 | CH$_3$ | S | CH$_2$OAc | mix | same as above |
| 3 | ![thienylethyl] | S | H | mix | same as above |
| 4 | same | S | CH$_2$OAc | mix | same as above |
| 5 | same | SO | H | cis | same as above |
| 6 | same | SO | H | trans | same as above |
| 7 | same | SO | CH$_2$OAc | mix | same as above |
| 8 | same | SO$_2$ | H | mix | same as above |
| 9 | same | SO$_2$ | CH$_2$OAc | mix | same as above |
| 10 | same | SO | CHPh$_2$ | mix | ![chlorobromoindole] |

The cephalosporin starting materials are commercially available cephalosporin derivatives 7-aminocephalosporanic acid or 7-amino 3'-chlorocephalosporanic acid as its benzhydryl or tertiaryy butyl ester ($R_0$).

A large variety of phenolic fluorophores could be substituted for the resorufin derivative disclosed herein. Examples include the courmarin, the pyrene, and the rhodol. Further examples are discussed in U.S. Pat. No. 5,741,657, hereby incorporated by reference in its entirety. In each case the fluorescence is greatly enhanced and shifts to longer wavelengths when the free phenolic group is release from the ether linkage to the cephalosporin.

Another variety of fluorophore formation is exemplified by the fluorosalicylate ether. Once the free fluorosalicylate is released it forms a mixed chelate with terbium-EDTA or europium-EDTA, which would be provided as an additional component of the assay system. Excitation of the fluorosalicylate causes energy transfer to the lanthanide ion, which then emits with extremely sharp peaks and millisecond-long fluorescence lifetimes. Both the latter properties make this fluorescence very distinctive and easy to separate from autofluorescence backgrounds.

A chemiluminescence readout can also be generated by use of the adamantylidene-dioxetane. The release of the free phenol triggers spontaneous fragmentation of the dioxetane and emission of light. Another version is the luciferin ether. In this case ATP is added and luciferase to get the light output. Only free luciferin, not a luciferin derivative is a substrate for the enzyme. The advantage over the adamanylidene-dioxetane would be the much higher quantum efficiency of the luciferase-catalyzed chemiluminescence compared to the non-enzymatic glow.

Colored or fluorescent precipitates should result from the indolyl or 2-(2-hydroxyphenyl)quinazolin-4-one substrates. Release of the free phenol triggers oxidation of 3-hydroxyindoles to blue indigo precipitates. The free 2-(2-hydroxyphenyl)quinazolin-4-one likewise forms a brightly fluorescent precipitate.

It is also possible to couple two cephalosporins to a bis(phenol) such as the fluorescein. Only when both phenols are freed does the fluorescein become fully fluorescent in such compounds.

The cephalosporin backbone serves as a cleavable linker. After cleavage it provides the charges necessary to keep a dye inside the cell. As discussed above, a compound of general formula 1 may have a single fluorophore or chromophore. The fluorophore or chromophore is quenched in the intact molecule, and the fluorescence properties of the molecules change upon enzymatic cleavage. For example, in embodiments of the compounds disclosed herein, having vinylogous cephalosporins as shown in general formula 1, fluorescence typically increases upon enzyme cleavage. Alternatively, in embodiments of the compounds disclosed herein, fluorescence may decrease upon enzyme cleavage.

Where the compound includes two or more fluorophores or chromophores, dyes may be chosen in a manner that one dye absorbs light (quencher or acceptor chromophore) at the wavelength that the other one emits (donor fluorophore). In the intact cephalosporin the two dyes are in close proximity to each other. When exciting the donor fluorophore one observes fluorescence resonance energy transfer (FRET) from the donor to the acceptor instead of donor fluorescence (Forster, T., Ann. Physik 2:55-75 (1948)). If the acceptor is a nonfluorescent dye the energy is given off to the solvent; the donor fluorescence is quenched. In the case of the acceptor being itself a fluorescent dye, fluorescence re-emission occurs at the acceptor's emission wavelength. In polar solvents such as water, hydrophobic donor and acceptor fluorophores can stack when separated by a short flexible linker. Due to this association in the ground state, a dark complex is formed (Yaron, A. et al., Anal. Biochem. 95: 228-235 (1979)). In this complex, neither fluorophore can emit light, causing the fluorescence of both dyes to be quenched (Bojarski, C. and Sienicki, K. Energy transfer and migration in fluorescent solutions. In: Photochemistzy and Photophysics, edited by Rabek, J. F. Boca Raton: CRC Press, Inc., 1990, pp. 1-57). In either case, a large change in fluorescence goes along with beta-lactam cleavage, which can be used to measure beta-lactamase activity. As both dyes diffuse away from each other, stacking and energy transfer are disrupted. Cephalosporins carrying a donor and an acceptor dye which fluoresces are referred to herein as FRET-cephalosporins.

Fluorescence resonance energy transfer has been used as a spectroscopic ruler for measuring molecular distances in proteins and peptides as it is effective in the range from 10-100 angstroms. This energy transfer is proportional to the inverse sixth power of the distance between donor and acceptor. Its efficiency is higher, the better donor emission and acceptor absorbance overlap, and the longer the fluorescence lifetime of the donor (in absence of the acceptor). FRET can be very efficient over distances of 10-20 angstroms.

In an embodiment in which a cephalosporin comprises multiple fluorophores or chromophores, distances for attachment of donor and acceptor are greater than 10 angstroms and a minimum of 10 bond-lengths, if one includes the two minimal spacers at 7- and 3-positions. Over this distance FRET is very efficient, if the right donor-acceptor pairs are chosen. Upon cleavage, fluorescence increases due to loss of the quencher dye.

The fluorogenic substrates of the invention are typically initially colorless and nonfluorescent outside cells. The substrates are designed so they readily cross cell membranes into the cytoplasm, where they are converted to fluorescent compounds by endogenous nonspecific esterases and stay trapped due to their charges. In the intact molecules, fluorescence energy transfer occurs leading to fluorescence at a particular wavelength when the substrates are excited. Lactamase cleavage of the beta-lactam ring is followed by expulsion of the fluorescein moiety, which expulsion is detectable (e.g., fluorescence may increase with loss of quenching of a single chromophore, or with loss of fluorescence energy transfer where two or more fluorophores are present). Excitation of the modified substrate now results in fluorescence at a different wavelength or results in an increase in detected fluorescence.

The assay systems of the present invention further provide an advantageous and rapid method of isolation and clonal selection of stably transfected cell lines containing reporter genes and having the desired properties which the transfection was intended to confer, e.g., fluorescent signal response after activation of a transfected receptor with a high signal-to-noise ratio from a high proportion of isolated cells. Current procedures for clonal selection of satisfactorily transfected, genetically engineered cells from the initial population, are done mainly by replica plating of colonies, testing of one set of colonies, visual selection of preferred clones, manual isolation of the replicas of the preferred clones by pipetting, and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system can be maintained within living and viable cells. Replica plating of colonies is unnecessary because single cells can be assayed and remain viable for further multiplication. Thus, from the population of initially transfected cells, one can rapidly select those few individual living cells with the best fluorescent signal, using automated instruments such as a fluorescent-activated cell sorter, e.g., the Becton Dickinson FACS Vantage™. The selected cells are then collected for cultivation and propagation to produce a clonal cell line with the desired properties for assays and drug screening.

As would be immediately apparent to those working in the field, the combination of a novel substrate in accordance with the invention and a suitable beta-lactamase may be employed in a wide variety of different assay systems (such as are described in U.S. Pat. Nos. 4,740,459 and 5,955,604). In particular, the fluorogenic substrates of the invention enable the detection of beta-lactamase activity in a wide variety of biologically important environments, such as human blood serum, the cytoplasm of cells and intracellular compartments; this facilitates the measurement of periplasmic or secreted beta-lactamase.

Further, the expression of any target protein can be detected by fusing a gene encoding the target protein to a beta-lactamase gene, which can be localized by immunostaining and fluorescence or electron microscopy. For example, beta-lactamase fusion proteins may be detected in the lumen of organelles through the use of the substrates of the invention; only subcellular compartments containing the fusion protein fluoresce at a wavelength characteristic of the cleaved substrate, whereas all others fluoresce at a wavelength characteristic of the intact molecule.

Both the intact and cleaved substrate are well retained in cells without the use of special measures, such as chilling. The color change (even in individual small mammalian cells) is visible through a fluorescence microscope using normal color vision or photographic film; the fluorescence signal may be quantified and further enhanced by conventional digital image processing techniques. Moreover, because gene activation is detected not by a change in a single intensity but rather by a color change or a change in the ratio between two intensities at different wavelengths, the assays of the present invention are relatively immune to many artifacts such as variable leakiness of cells, quantity of substrate, illumination intensity, absolute sensitivity of detection and bleaching of the dyes.

A variety of substrates (e.g., the compounds above and in Table 1) have been prepared and their emission spectra can be obtained before and after beta-lactamase cleavage. These substrates allow for beta-lactamase detection primarily in vitro, as they bind strongly to serum and cellular proteins. Due to their hydrophobic nature, the fluorophores stack; this leads to a loss of fluorescence in the intact substrate. beta-lactamase cleaves the substrates and relieves the stacking, allowing for fluorescence.

The substrates of this invention make it feasible to use beta-lactamase as a reporter gene to monitor the expression from a set of expression control sequences. In one aspect, this invention provides methods for monitoring gene expression from a set of expression control sequences by using beta-lactamase as a reporter gene. A cell is provided that has been transfected with a recombinant nucleic acid molecule comprising the expression control sequences operably linked to nucleic acid sequences coding for the expression of beta-lactamase.

As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

Nucleic acids encoding beta-lactamases can be obtained by methods known in the art, for example, by polymerase chain reaction of cDNA using primers based on the DNA sequence known in the art and disclosed in U.S. Pat. No. 5,955,604, which is incorporated herein by reference). PCR methods are described in, for example, U.S. Pat. No. 4,683,195; Mullis et al. (1987) Cold Spring Harbor Symp. Quant. Biol. 51:263; and Erlich, ed., PCR Technology, (Stockton Press, N.Y., 1989).

The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., (most recent Supplement)).

Nucleic acids used to transfect cells with sequences coding for expression of the polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the are recognizes, this includes all degenerate nucleic acid sequences encoding the same amino acid sequence. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The recombinant nucleic acid used to transfect the cell contains expression control sequences operably linked to a nucleotide sequence encoding a beta-lactamase. The beta-lactamase encoded can be any known to the art or described herein.

This invention provides novel recombinant nucleic acid molecules including expression control sequences adapted for function in a non-mammalian eukaryotic cell operably linked to a nucleotide sequence coding for the expression of a cytosolic beta-lactamase. As used herein, "cytosolic beta-lactamase" refers to a beta-lactamase that lacks amino acid sequences for secretion from the cell membrane, e.g., the signal sequence.

It is further preferable that the ribosome binding site and nucleotide sequence coding for expression of beta-lactamase contain sequences preferred by mammalian cells. Such sequences improve expression of beta-lactamase in mammalian cells. Preferred sequences for expression in mammalian cells are described in, for example, Kozak, M., J. Cell Biol. 108.

When used in mammalian cells, the expression control sequences are adapted for function in mammalian cells. The method of this invention is useful to testing expression from any desired set of expression control sequences. In particular, this invention is useful for testing expression from inducible expression control sequences. As used herein, "inducible expression control sequences" refers to expression control sequences which respond to biochemical signals either by increasing or decreasing the expression of sequences to which they are operably linked. For example, in the case of genes induced by steroid hormones, the expression control sequences includes hormone response elements. The binding of a steroid hormone receptor to the response element induces transcription of the gene operably linked to these expression control sequences. Expression control sequences for many genes and for inducible genes, in particular, have been isolated and are well known in the art. The invention also is useful with constitutively active expression control sequences.

The transfected cell is incubated under conditions to be tested for expression of beta-lactamase from the expression control sequences. The cell or an extract of the cell is contacted with a beta-lactamase substrate of the invention under selected test conditions and for a period of time to allow catalysis of the substrate by any beta-lactamase expressed. Then the donor moiety from this sample is excited with appropriate ultraviolet or visible wavelengths. The degree of fluorescence resonance energy transfer in the sample is measured.

If the cell did not express beta-lactamase, very little of the substrate will have been cleaved, the fluorescence of a single fluorophore or chromophore will be low, and (where multiple fluorpohores or chromophores are present) efficiency of FRET in the cell will be high, and the fluorescence characteristics of the cell or sample from it will reflect this situation. If the cell expressed a large amount of beta-lactamase, most of the substrate will be cleaved. In this case, the fluoreacent characteristics of the fluorophore or chromophore of compounds having a single chromophore or fluorophore will be altered, or, where there are multiple chromophores or fluorophores, efficiency of FRET is low, reflecting a large amount or high efficiency of the cleavage enzyme relative to the rate of synthesis of the tandem fluorescent protein construct. In one aspect, this method can be used to compare mutant cells to identify which ones possess greater or less enzymatic activity. Such cells can be sorted by a fluorescent cell sorter based on fluorescence.

Also, as will be apparent to those working in the field of using reporter gene cell-based assays for screening samples or pools of samples (such as compounds (combinatorial or synthetic), natural product extracts, or marine animal extracts) to identify potential drug candidates which act as agonists, inverse agonists or antagonists of cellular signaling or activation, the combination of cells (preferably mammalian) genetically engineered to express beta-lactamase under the control of different regulatory elements/promoters and the use of the novel beta-lactamase substrate compounds of the present invention will provide distinct advantages over known reporter genes (including, but not limited to, chloramphenicol acetyl transferase, firefly luciferase, bacterial luciferase, vargula luciferase, aequorin, beta-galactosidase, alkaline phosphatase) and their requisite substrates.

By the choice of appropriate regulatory elements and promoters to control expression of beta-lactamase, assays can be constructed to detect or measure the ability of test substances to evoke or inhibit functional responses of intracellular hormone receptors. These include expression control sequences responsive to inducible by mineralcorticosteroids, including dexamethasone (J. Steroid Biochem. Molec. Biol. Vol. 49, No. 1 1994, pp. 31), gluococorticoid, and thyroid hormone receptors (as described in U.S. Pat. No. 5,071,773). Additional such intracellular receptors include retinoids, vitamin D3 and vitamin A (Leukemia vol 8, Suppl. 3, 1994 pp S1-S10; Nature Vol. 374, 1995, p. 118-119; Seminars in Cell Biol., Vol. 5, 1994, p. 95-103). Specificity would be enabled by use of the appropriate promoter/enhancer element. Additionally, by choice of other regulatory elements or specific promoters, drugs which influence expression of specific genes can be identified. Such drugs could act on specific signaling molecules such as kinases, transcription factors, or molecules such signal transducers and activators of transcription (Science Vol. 264, 1994, p. 1415-1421; Mol. Cell Biol., Vol. 16, 1996, p. 369-375). Specific microbial or viral promoters which are potential drug targets can also be assayed in such test systems.

Also by the choice of promoters such as c-fos or c-jun (U.S. Pat. No. 5,436,128; Proc. Natl. Acad. Sci. Vol. 88, 1991, pp. 5665-5669) or promoter constructs containing regulatory elements responsive to second messengers (Oncoqene, 6:745-751 (1991)) (including cyclic AMP-responsive elements, phorbol ester response element (responsive to protein kinase C activation), serum response element (responsive to protein kinase C-dependent and independent pathways) and Nuclear Factor of Activated T-cells response element (responsive to calcium) to control expression of beta-lactamase, assays can be constructed to detect or measure substances or mixtures of substances that modulate cell-surface receptors including, but not limited to, the following classes: receptors of the cytokine superfamily such as erthyropoietin, growth hormone, interferons, and interleukins (other than IL-8) and colony-stimulating factors; G-protein coupled receptors (U.S. Pat. No. 5,436,128) for hormones, such as calcitonin, epinephrine or gastrin, pancrine or autocrine mediators, such as stomatostatin or prostaglandins, and neurotransmitters such as norepinephrine, dopamine, serotonin or acetylcholine; tyrosine kinase receptors such as insulin growth factor, nerve growth factor (U.S. Pat. No. 5,436,128). Furthermore, assays can be constructed to identify substances that modulate the activity of voltage-gated or ligand-gated ion channels, modulation of which alters the cellular concentration of second messengers, particularly calcium (U.S. Pat. No. 5,436,128). Assays can be constructed using cells that intrinsically express the promoter, receptor or ion channel of interest or into which the appropriate protein has been genetically engineered.

The expression control sequences also can be those responsive to substances that modulate cell-surface receptors or that modulate intra-cellular receptors.

To measure whether a substance or mixture of substances activates extracellular or intracellular receptors or other cellular responses, cells containing beta-lactamase controlled by a desired promoter/enhancer element are incubated with test substance(s), substrate then added, and after a certain period of time the fluorescence signal is measured at either one or two excitation-emission pairs appropriate to the chosen compound of the invention (e.g., compound CCF2 with wavelength pairs of near 405 nm and near 450 nm and near 405 and near 510 nm). This fluorescent result is compared to control samples which have had no drug treatment and, when feasible, control samples with a known inhibitor and a known activator. The effect of any active drugs is then determined using the ratio of the fluorescence signal found in test wells to the signals found in wells with no drug treatment. Assays are performed in wells in a microtiter plate containing 96 or more wells or in an assay system with no compartments such as a gel matrix or moist membrane environment. Detection could be done for example by microtiter plate fluorimeters, e.g., Millipore Cytofluor, or imaging devices capable of analyzing one or more wells or one or more assay points in a certain surface area, e.g., as supplied by Astromed. The ability to retain the substrate in the cytoplasm of living cells is advantageous as it can allow a reduction in signal interference from coloured or quenching substances in the assay medium. Furthermore, the fluorescent signal from the compounds of this invention, such as CCF2, can be readily detected in single cells and thus allowing assay miniaturization and an increased number of tests per surface area. Miniaturized assays also further increase the throughput of an imaging detection system as there are more samples within the imaging field.

The assay systems of the present invention further provide an advantageous and rapid method of isolation and clonal selection of stably transfected cell lines containing reporter genes and having the desired properties which the transfection was intended to confer, e.g., fluorescent signal response after activation of a transfected receptor with a high signal-to-noise ratio of at least 10:1 from a high proportion of isolated cells. Current procedures for clonal selection of satisfactorily transfected, genetically engineered cells from the population initial transfected with the vectors of interest, are done mainly by manual means and involve several rounds of microscopic analyses, selecting the visually preferred clone, isolation of the clone by manual pipetting stages and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system can be maintained within living and viable cells. Thus, one can rapidly select, from the population of initially transfected cells, those few living cells with the best fluorescent signal using automated instruments such as a fluorescent-activated cell sorter, e.g., the Becton Dickinson FACS Vantage. The selected cells are then collected for cultivation and propagation to produce a clonal cell line with the desired properties for assays and drug screening.

In addition, the presence (for example, in human serum, pus or urine) of bacteria resistant to beta-lactam antibiotics can be readily detected using the substrates of the present invention. Only in the presence of an active beta-lactamase is there a change in the fluorescence spectrum from that of the intact molecule to one characteristic of the cleavage product. The substrates of the present invention are superior to prior art chromogenic substrates Nitrocephin and PADAC, in that the inventive substrates are stable to human serum. The novel substrates are also more sensitive than the chromogenic substrate CENTA, because they experience a much smaller optical background signal from human serum and a lower detection limit for fluorescence versus absorbance.

The invention may be better understood with reference to the accompanying examples, which are intended for purposes of illustration only and should not be construed as in any sense limiting the scope of the invention as defined in the claims appended hereto.

The degree of FRET or amount of fluorescence can be determined by any spectral or fluorescence lifetime characteristic of the excited construct, for example, by determining the intensity of the fluorescent signal from the donor, the intensity of fluorescent signal from the acceptor or quencher, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of fluorescence or FRET are determined, for example, as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore, the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of lanthanide complexes in which case microsecond to millisecond resolution is sufficient.

Fluorescence in a sample is measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modem Molecular Photochemistry, Menlo Park: Benjamin/Cummings Publishing Col, Inc. (1978), pp. 296-361.

The Figures and figure legends attached hereto depict assays based upon the methods and substrates identified above.

In general, it is desirable that the compounds of general formula 1 are membrane-permeant by derivatizing them to render them hydrophobic and permeable through cell membranes. Ideally, the derivatizing groups should undergo hydrolysis inside cells to regenerate the compounds of general formula 1 and trap them inside the cells. Therefore, any free amines of the compounds of general formula 1 may be acylated to give an acyl substituent (e.g., acetyl) or converted to various other esters and carbonates (see, Bundgaard, H., Design of Prodrugs, Elsevier Science Publishers (1985), Chapter 1, page 3 et seq.). Likewise, any carboxyls or —$SO_3H$ of the compounds of general formula 1 may be esterified to give, among others, —O-alkyl and —O-aliphatic ester substituents. The carboxyl and —$SO_3H$ may be esterified with 1-(acyloxy)alkyl, acylthiomethyl, acyloxy-alpha-benzyl, delta-butyrolactonyl, methoxycarbonyloxymethyl, methylsulfinylmethyl, beta-morpholinethyl, 2-(dimethylamino)ethyl, 2-(diethylamino)ethyl, or dialkylaminocarbonyloxymethyl groups as discussed in Ferres, H. (1980) Chem. Ind. 1980: 435-440. A preferred esterifying group for the carboxyl is acetoxymethyl.

Generally, compounds having formula 1 can be made following the general procedures illustrated in Examples 1 through 3. Preferred starting materials and products for the reactions for producing compounds of general formula 1 are set forth in Examples 1-3. When compounds of the general formula 1 (or its membrane permeant derivative) interact with an appropriate beta-lactamase enzyme, the beta-lactam ring is cleaved, resulting in the product after being cleaved by a beta-lactamase. The resulting cleaved compound can have a carboxyl group that, at physiological pH, will be charged. As a consequence, the cleaved compound will have better intracellular retention than its parent compound.

The starting material, product, and product after being cleaved by a beta-lactamase can be non-fluorescent, short-wavelength fluorescent (meaning, for this purpose, that the excitation and/or emission wavelengths of the product are shorter than those of the starting material) or long-wavelength fluorescent (meaning, for this purpose, that the excitation and/or emission wavelengths of the product are equal to or longer than those of the starting material). Compounds of general formula 1 (and their membrane permeant derivatives) will have different fluorescent properties from their fluorophore precursor. Formation of the beta-lactam ring will shift the fluorescence of the fluorophore precursor to shorter wavelength or even abolishes their fluorescence. Cleavage of the beta-lactam will essentially restore the fluorescence of the fluorophore precursor (in some embodiments, with some possible differences that are attributable to the propionic acid moiety that is attached to what was previously a primary amine in the fluorophore precursor).

Figure 11A:
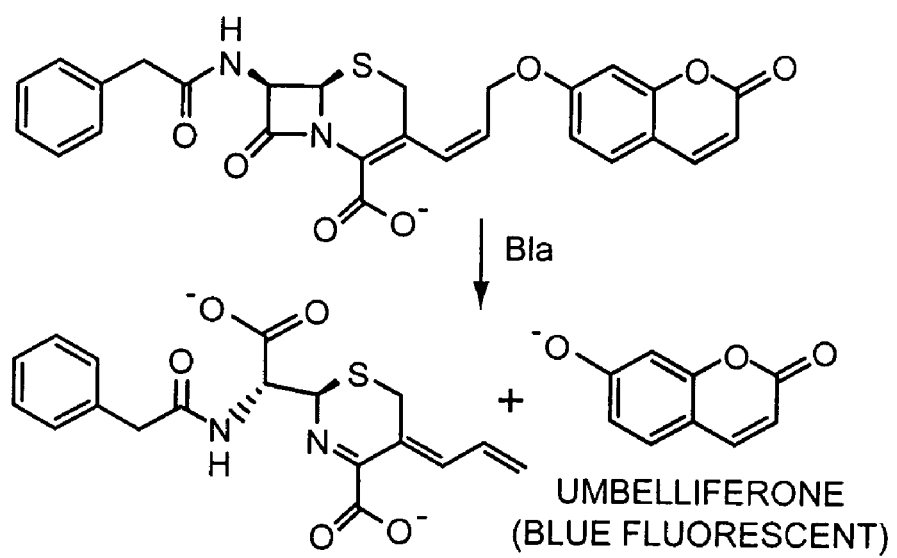
FIG. 11A shows that hydrolysis of CC1 by β-lactamase releases the fluorophore umbelliferone.
Figure 11B:
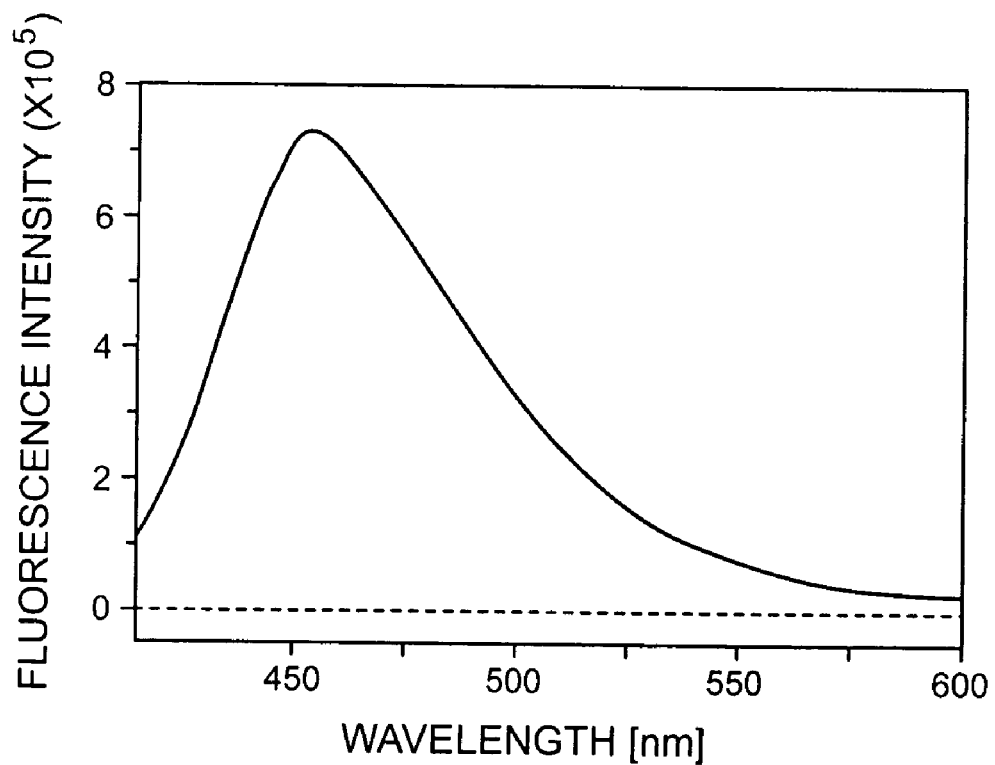
FIG. 11B shows the emission spectrum of CC1 before (dash dot line) and after (solid line) treatment of β-lactamase (excitation at 400 μm).
Figure 12:
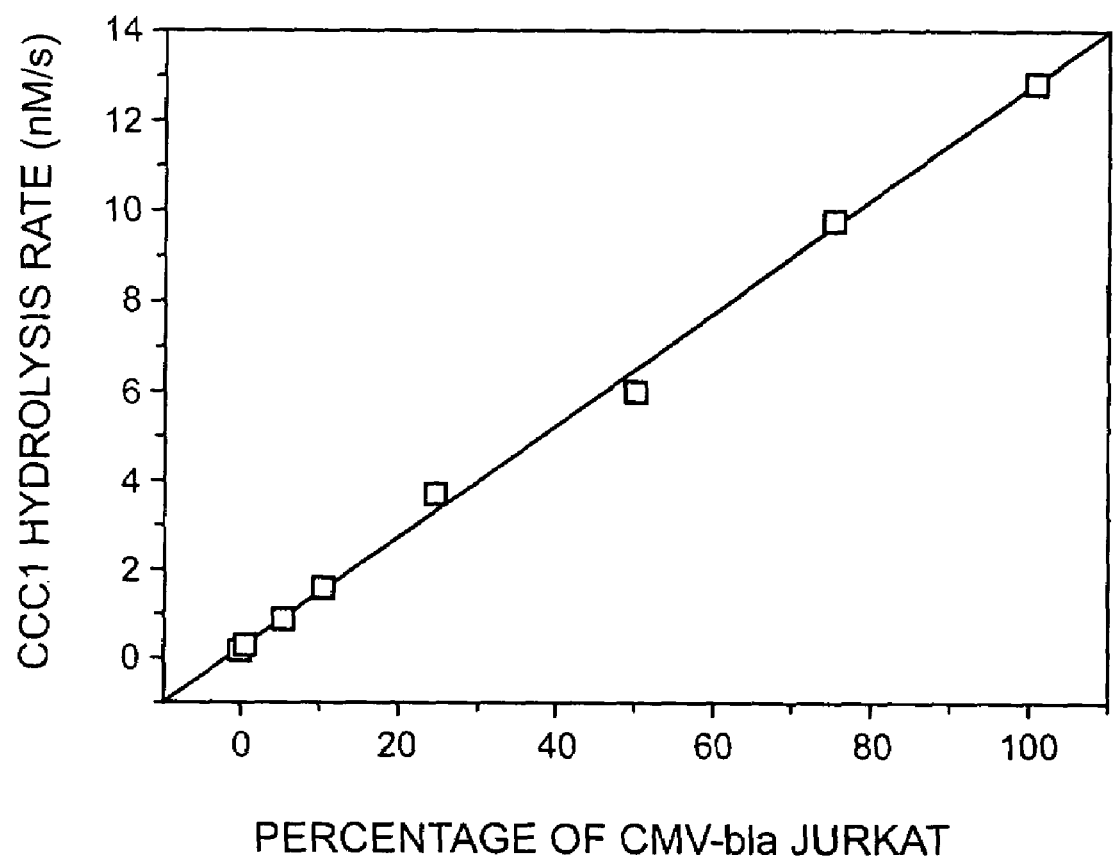
FIG. 12 illustrates the linear nature of the dependence of the CC1 hydrolysis rate on the β-lactamase concentration.

A class of compounds useful in the practice of the invention includes β-lactam compounds where a phenolate is linked to a vinylogous cephalosporin, effective that cleavage of the β-lactam ring by β-lactamase releases a phenolate from the vinylogous cephalosporin. Cleavage of the β-lactam ring of a cepphalosporin creates a free amino group, which triggers spontaneous elimination of any leaving group previously attached to the 3' position. A suitable leaving group may be, for example, umbelliferone, which fluoresces with an excitation peak of 360 nm with peak emission at 460 nm. When alkylated at the 7-hydroxy position, however, umbelliferone becomes essentially non-fluorescent. A β-lactam compound including an umbelliferone moiety, CC1, was designed and synthesized in which the 3' position of a cephalosporin is linked to the 7-hydroxy group of umbelliferone through an allylic ether bond. The synthesis of CC1 is described in Example 1, and is illustrated in Scheme 1 of that Example. The structure of compound CC1 is illustrated in FIG. 11A, and the emission spectrum of CC1 before and after cleavage to free the umbelliferone moiety is illustrated in FIG. 11B. As shown in FIG. 12, the hydrolysis rate of CC1 by β-lactamase depends linearly on the β-lactamase concentration. Wild-type and CMV-bla-Jurkat cells were mixed at different ratios (with the percentage of CMV-bla Jurkat cells from 0, 0.5, 1, 5, 10, 25, 50, 75, to 100%) lysed and diluted for CC1 assay with excitation at 365/42 nm and emission at 465/35 nm (where "excitation at 365/42 nm" indicates that the excitation peak was centered at 365 nm with a half-width (also termed "bandwidth") of 42 nm around that peak, and "emission at 465/35 nm" indicates that the emission peak was centered at 465 nm with a half-width of 35 nm around that peak).

Beta-lactamase Enzymes

Beta-lactamase enzymes are a class of enzymes that have been characterized because of their clinical relevance in making bacteria resistant to beta-lactam antibiotics (see, Waley, S. G., Sci. Prog. 72: 579-597 (1988); Richmond, M. H. et al., Ann. N.Y. Acad. Sci. 182: 243-257 (1971)). Many beta-lactamases have been cloned and their amino acid sequence determined (see, Ambler, R. P., Phil. Trans. R. Soc. Lond. (Ser.B.) 289: 321-331 (1980)).

A large number of beta-lactamase enzymes have been isolated and characterized, all of which may be suitable for use in accordance with the present invention. Initially, beta-lactamase enzymes were divided into different classes (I through V) on the basis of their substrate and inhibitor profiles and their molecular weight (see, Richmond, M. H. and Sykes, R. B., Adv.Microb.Physiol. 9: 31-88 (1973)). More recently, a classification system based on amino acid and nucleotide sequence has been introduced (see, Ambler, R. P., Phil. Trans. R. Soc. Lond. (Ser.B.) 289: 321-331 (1980)). Class A beta-lactamases possess a serine in the active site and have an approximate weight of 29 kd. This class contains the plasmid-mediated TEM beta-lactamases such as the RTEM enzyme of pBR322. Class B beta-lactamases have an active-site zinc bound to a cysteine residue. Class C enzymes have an active site serine and a molecular weight of approximately 39 kd, but have no amino acid homology to the class A enzymes.

The coding region of an exemplary beta-lactamase that could be employed in the reporter gene assays has been described and is available in pTG2dell (see, Kadonaga J. T. et al., J.Biol.Chem. 259: 2149-2154 (1984)). The entire coding sequence of wild-type pBR322 beta-lactamase has also been published (see, Sutcliffe, J. G., Proc.Natl.Acad.Sci.USA 75: 3737-3741 (1978)). As would be readily apparent to those skilled in the field, this and other comparable sequences for peptides having beta-lactamase activity would be equally suitable for use in accordance with the present invention. The beta-lactamase reporter gene is employed in an assay system in a manner well known per se for the use of reporter genes (for example, in the form of a suitable plasmid vector).

In addition, mutants of these beta-lactamase sequences can be prepared that may have a different specificity, i.e., mutants may cleave compounds of general formula 1 (or its membrane permeant derivative) that a naturally occurring beta-lactamase enzymes may not. Techniques for mutagenesis are well known in the art (Sambrook et al., Molecular Cloning, A Laboratory Manual, Cold Spring Harbor Laboratory Press (1989)). Numerous studies of site directed mutagenesis have been completed on beta-lactamase (Sigal et al. J. Biol. Chem. 259:5327-5332 (1984); Dalbadies-McFarland et al. Biochemistry 25:332-338 (1986); Schultz and Richards, Proc. Natl. Acad. Sci. USA 83:1588-1592 (1986); Madgwick et al., Biochem. J. 248:657-662 (1987); Ellerby et al. Biochemistry 29:5797-5806 (1990); Gibson et al. Biochem. J. 272:613-619 (1990); Jacob et al. Biochem. J. 271 :399-406 (1990); Lenfant et al. Biochimie 72:495-503 (1990); Adachi et al. J. biol. Chem. 266:3186-3191 (1991); Escobar et al. Biochemistry 30:10783-10787 (1991); Jacob-Dubuisson et al. Protein Eng. 4:811-819 (1991); Juteau et al. Biotechniques 11:460-462 (1991); Lenfant et al. J. Biol. Chem. 266:17187-17194 (1991); Delaire et al. J. Biol. Chem. 267:20600-20606 (1992); Juteau et al. Prot. Eng. 5:693-701 (1992); Lamotte- Brasseur et al. Biochem. J. 282:189-195 (1992); Thornewell and Waley, Biochem. J. 288:1045-1051 (1992); Zafaralla et al. Biochemistry 31:3874-3852 (1992); Knox et al. Protein Eng. 6:11-18 (1993); Lenfant et al. Eur. J. Biochem. 217:939-946 (1993)).

In addition, some single point mutations created functional enzymes with drastically altered substrate specificities (see, Collatz et al. Gene 78:349-354 (1989); Palzkill and Botstei, J. Bacteriol. 5237-5243 (1992); Jacob et al. Protein Eng. 4:79-86 (1990); Sowek et al. Biochemistry 30:3179-3188 (1991); Delaire et al. Protein Eng. 4:805-810 (1991); Healey et al. Proteins 6:275-283 (1989); Lee et al. Proteins 11:45-51 (1991)).

A variety of random mutagenesis techniques have also been used to mutate beat-lactamase enzymes (see, Oliphant and Struhl, Proc. Natl. Acad. Sci. USA 86:9094-9089 (1989); Shortle et al. Proc. Natl. Acad. Sci. USA 77:5375-5379 (1980); Dalbadie-McFarland et al. Proc. Natl. Acad. Sci. USA 79:6409-6413 (1982); Shortle and Botstein, Basic. Life Sci. 20:147-155 (1982); Dalbadie-McFarland et al. Biochem. Soc. Trans. 12:226-228 (1984); Barany, Proc. Natl. Acad. Sci. USA 82:4202-4206 (1985); Barany, Gene 37:111-123 (1985); Kadonaga and Knowles, Nucleic Acids Res. 13:1733-1745 (1985); Foster et al. J. Bacteriol. 169:2476-2481 (1987); Anthony-Cahill et al. Trends Biochem. Sci. 14:400-403 (1989); Zebala and Barany, Gene 100:51-57 (1991); Palzkill and Botstein, Proteins 14:29-44 (1992)).

Assays

The compounds of general formula 1 (or its membrane permeant derivative) have advantages over other types of fluorescent compounds in reporter gene assays. Most notably, this invention does not rely on fluorescent resonant energy transfer (FRET) between a donor and acceptor molecule in the assay (for FRET, see, WO 96/30540, to Tsien, published Oct. 3, 1996). Because quenching between a donor and acceptor molecule is rarely entirely complete, gene reporter systems that use FRET have background signals that may reduce the sensitivity of their assays. In contrast, the compounds of general formula 1 (or its membrane permeant derivative), when used in a reporter gene assay, have negligible background. The compounds of general formula 1 (or its membrane permeant derivative) fluoresce upon excitation with light of the proper wavelength only if a beta-lactamase enzyme has cleaved the beta-lactam ring. Because of the reduced background signal, the compounds of general formula 1 (or its membrane permeant derivative) may give a more sensitive reporter gene assay.

The interaction of a particular compound of general formula 1 (or their membrane-permeant derivative) with a particular beta-lactamase enzyme can be readily determined. The method involves contacting the sample with a compound having general formula 1 (or its membrane-permeant derivative), exciting at one or more wavelengths that are suitable for the cleaved compound, and determining the degree of fluorescence in the sample. A degree of fluorescence that is greater than an expected amount indicates that the particular beta-lactamase enzyme can cleave the particular compound having the general formula 1 (or its membrane-permeant derivative). The amount of fluorescence expected can be determined using, for example, a control sample, or control values determined contemporaneously, prior to, or after a particular assay was performed. Such expected values can include a statistical analysis, such as a mean and standard deviation, to provide a chosen statistical confidence level. Both naturally occurring beta-lactamase enzymes and beta-lactamase enzymes prepared by mutagenesis can be tested with a particular compound having the general formula 1 (or their membrane-permeant derivatives). A particular compound having the general formula 1 (or its membrane permeant derivative) is a substrate for the particular beta-lactamase enzyme that cleaved the beta-lactam ring.

Even if a particular compound of general formula 1 (or its membrane-permeant derivative) is not cleaved by a naturally occurring beta-lactamase enzyme, the particular compound of general formula 1 or a membrane-permeant derivative thereof may have value as an inhibitor of the naturally-occurring beta-lactamase enzyme. The ability of a compound to inhibit a beta-lactamase can be confirmed using methods set forth in the present invention. For example, samples comprising beta-lactamase activity can be contacted with a compound of the present invention, and further contacted with a substrate for beta-lactamase. An amount of beta-lactamase activity less than expected indicates that the compound inhibits beta-lactamase activity. The expected level of activity can be determined using a proper control or historical values, or other methods known in the art.

The assay systems of the present invention provide an advantageous and rapid method of isolation and clonal selection of stably transfected cell lines containing reporter genes and having the desired properties which the transfection was intended to confer, e.g., fluorescent signal response after activation of a transfected receptor with a high signal-to-noise ratio from a high proportion of isolated cells. Current procedures for clonal selection of satisfactorily transfected, genetically engineered cells from the initial population, are done mainly by replica plating of colonies, testing of one set of colonies, visual selection of preferred clones manual isolation of the replicas of the preferred clones by pipetting, and prolonged cellular cultivations. This procedure is laborious and time-consuming, and it may require several months to generate a clone useful for assays suited to drug screening. Moreover, it is difficult to manually select and maintain more than a few hundred clones.

Using the assays of this present invention, the desired signal from cellular beta-lactamase reporter system can be maintained within living and viable cells. Replica plating of colonies can be unnecessary because single cells cam be assayed and remain viable for later culturing and expansion. Thus, from a population of initially transfected cells, an artisan can rapidly select those few individual living cells with the best fluorescent signal using automated instruments such as a fluorescent-activated cell sorter (e.g., the Becton Dickinson FACS Vantage™). The selected cells can then be collected for culturing and expansion to produce a clonal cell line with the desired properties for assays and drug screening.

As would be immediately apparent to those working in the field, the combination of a substrate of this invention and a suitable beta-lactamase enzyme can be used in a wide variety of different assay systems (see, e.g., U.S. Pat. No. 4,740,459). In particular, the substrates of the invention can enable the detection of beta-lactamase activity in a wide variety of biologically important environments, such as human blood serum, the cytoplasm of cells and intracellular compartments, which can facilitate the measurement of periplasmic or secreted beta-lactamase enzyme.

Further, the expression of any target protein may be detected by fusing a gene encoding the target protein to a beta-lactamase gene, which can be localized by immunostaining or fluorescence or electron microscopy. For example, beta-lactamase fusion proteins can be detected in the lumen of organelles through the use of the substrates of the invention. In this instance, only subcellular compartments containing the fusion protein fluoresce at a wavelength characteristic of the cleaved substrate, whereas all others fluoresce at a wavelength characteristic of the intact molecule.

Both the intact and cleaved substrate can be efficiently retained in cells without the use of special measures, such as chilling. The change in fluorescence of the compound caused by cleavage by a beta-lactamase (even in individual small mammalian cells) can be visible through a fluorescence microscope using normal color vision or photographic film. In addition, the fluorescence signal can be quantified and further enhanced by conventional digital image processing techniques.

Monitoring Gene Expression

The compounds of general formula 1 (or its membrane permeant derivative) may make it feasible to use beta-lactamase as a reporter gene to monitor the expression of a protein from a set of expression control sequences. In one aspect, this invention provides methods for monitoring gene expression from a set of expression control sequences by using beta-lactamase as a reporter gene.

Recombinant Nucleic Acids

As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

Nucleic acids encoding beta-lactamases can be obtained by methods known in the art, for example, by polymerase chain reaction of cDNA using primers based on the DNA sequence of a beta-lactamase (for PCR methods, see U.S. Pat. No. 4,683,195; Mullis et al. (1987) Cold Spring Harbor Symp. Quant. Biol. 51:263; and Erlich, ed., PCR Technology, (Stockton Press, N.Y., 1989). In addition, beta-lactamase enzymes can be prepared by mutagenesis using methods known in the art to produce variants of wild-type beta-lactamases.

The construction of expression vectors and the expression of genes in transfected cells uses molecular cloning techniques known in the art (see, Sambrook et al., Molecular Cloning—A Laboratory Manual, Cold Spring Harbor Laboratory, Cold Spring Harbor, N.Y., (1989); and Current Protocols in Molecular Biology, F. M. Ausubel et al., eds., (Current Protocols, a joint venture between Greene Publishing Associates, Inc. and John Wiley & Sons, Inc., ). The choice of the parent expression vector is one within the skill of the artisan based on known factors, such as the organism into which the expression vector is to be placed. The insertion of nucleic acid sequences encoding beta-lactamase activity into the expression vector in an appropriate orientation is also known in the art, as is the ability to insert such sequences into particular locations within the vector.

Nucleic acids used to transfect cells with sequences coding for expression of a polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the are recognizes, this includes all degenerate nucleic acid sequences encoding the same amino acid sequence. This can include sequences containing, e.g., introns.

As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences. These expression control sequences can be operativley linked to the recombinant nucleic acids, which can encode a beta-lactamase activity. The expression vector can be adapted for function in prokaryotes or eukaryotes by inclusion of appropriate promoters, replication sequences, markers, codons, and the like as is known in the art.

One aspect of the invention provides novel recombinant nucleic acid molecules including expression control sequences adapted for function in a mammalian or non-mammalian eukaryotic cell operably linked to a nucleotide sequence coding for the expression of a cytosolic beta-lactamase enzyme. As used herein, "cytosolic beta-lactamase enzyme" refers to a beta-lactamase enzyme that lacks amino acid sequences for secretion from the cell membrane (e.g., the signal sequence). This invention provides recombinant nucleic acid molecules including expression control sequences adapted for function in a mammalian or non-mammalian eukaryotic cell operably linked to a nucleotide sequence coding for the expression of a beta-lactamase enzyme.

It may be preferable that the ribosome binding site and nucleotide sequence coding for expression of a beta-lactamase enzyme contain sequences preferred by the host cells, such as eukaryotic and mammalian cells. Such sequences improve expression of beta-lactamase in mammalian cells. Preferred sequences for expression in mammalian cells are described in, for example, Kozak, M., J. (Cell Biol. 108: 229-241(1989)), which are referred to herein as "Kozak sequences."

When used in mammalian cells, the expression control sequences are adapted for function in mammalian cells. The method of this invention is useful to testing expression from any desired set of expression control sequences. In particular, this invention is useful for testing expression from inducible expression control sequences, such as those regulated by signal transduction. As used herein, "inducible expression control sequences" refers to expression control sequences that respond to biochemical signals either by increasing or decreasing the expression of sequences to which they are operably linked. For example, in the case of genes induced by steroid hormones, the expression control sequences includes hormone response elements. The binding of a steroid hormone receptor to the response element induces transcription of the gene operably linked to these expression control sequences. Expression control sequences for many genes, and for inducible genes in particular, have been isolated and are well known in the art. The invention also is useful with control sequences that control the constitutive expression of regulated proteins.

The transfected cell may be incubated under conditions to be tested for expression of a beta-lactamase enzyme from the expression control sequences. The cell or an extract of the cell is contacted with a substrate of this invention under selected test conditions and for a period of time to allow catalysis of the substrate by any beta-lactamase enzyme expressed. Then the cleaved substrate is excited with radiation of an appropriate wavelength, and the fluorescence emitted measured. If the cell did not express a beta-lactamase enzyme, very little of the substrate will have been cleaved, and there will be little fluorescence attributable to the cleaved compound. If the cell expressed a large amount of a beta-lactamase enzyme, most of the substrate will be cleaved, and there will be a great deal of fluorescence attributable to the cleaved substrate. In one aspect, this method can be used to compare mutant cells to identify which cells possess greater or less enzymatic activity. Such cells can be sorted using, for example, a fluorescent cell sorter based on fluorescence.

As will be apparent to those working in the field of reporter gene cell-based assays for screening samples or pools of samples (such as compounds (combinatorial or synthetic), natural products or extracts thereof, or marine animal extracts) to identify potential drug candidates which act as agonists, inverse agonists, or antagonists of cellular signaling or activation, the combination of cells (preferably mammalian) genetically engineered to express a beta-lactamase enzyme under the control of different regulatory elements/ promoters and the use of the substrates of this invention may provide distinct advantages over known reporter genes (including, but not limited to, chloramphenicol acetyl transferase, firefly luciferase, bacterial luciferase, Vargula luciferase, aequorin, beta-galactosidase, alkaline phosphatase) and their requisite substrates.

By choosing appropriate regulatory elements and promoters to control expression of a beta-lactamase enzyme, assays may be constructed to detect or measure the ability of test substances to evoke or inhibit functional responses of intracellular hormone receptors. These include expression control sequences responsive to inducible by mineralcorticosteroids, including dexanethasone (see, J. Steroid Biochem. Molec. Biol. Vol. 49, No. 1 1994, pp. 31-3), gluococorticoid, and thyroid hormone receptors (see, U.S. Pat. No. 5,071,773). Additional intracellular receptors include retinoids, vitamin D3 and vitamin A (see, Leukemia vol 8, Suppl. 3, 1994 pp S1-S10; Nature Vol. 374, 1995, p. 118-119; and Seminars in Cell Biol., Vol. 5, 1994, p. 95-103). Specificity of expression of the beta-lactamase can be accomplished by using the appropriate promoter/enhancer element. Additionally, by choice of other regulatory elements or specific promoters, drugs that influence expression of specific genes can be identified. Such drugs could act on specific signaling molecules such as kinases, transcription factors, or molecules such as signal transducers and activators of transcription (see, Science Vol. 264, 1994, p. 1415-1421; and Mol. Cell Biol., Vol. 16, 1996, p. 369-375). Specific microbial, parasitic or viral promoters or other regulatory sequences that are potential drug targets can also be assayed in such test systems.

Also by choosing promoters such as c-fos or c-jun (see, U.S. Pat. No. 5,436,128; and Proc. Natl. Acad. Sci. Vol. 88, 1991, pp. 5665-5669) or promoter constructs containing regulatory elements responsive to second messengers (see, Oncogene, 6: 745-751 (1991) (including cyclic AMP-responsive elements, phorbol ester response element (responsive to protein kinase C activation), serum response element (responsive to protein kinase C-dependent and independent pathways) and Nuclear Factor of Activated T-cells response element (responsive to calcium) to control expression of beta-lactamase enzyme, assays may be constructed to detect or measure substances or mixtures of substances that modulate cell-surface receptors including, but not limited to, the following classes: receptors of the cytokine superfamily such as erthyropoietin, growth hormone, interferons, and interleukins (other than IL-8) and colony-stimulating factors; G-protein coupled receptors (see, U.S. Pat. No. 5,436,128) for hormones, such as calcitonin, epinephrine or gastrin, pancrine or autocrine mediators, such as somatostatin or prostaglandins, and neurotransmitters such as norepinephrine, dopamine, serotonin or acetylcholine; tyrosine kinase receptors such as insulin growth factor, nerve growth factor (U.S. Pat. No. 5,436,128). Furthermore, assays may be constructed to identify substances that modulate the activity of voltage-gated or ligand-gated ion channels, modulation of which alters the cellular concentration of second messengers, particularly calcium (see, U.S. Pat. No. 5,436,128). Assays can be constructed using cells that intrinsically express the promoter, receptor or ion channel of interest or into which the appropriate protein has been genetically engineered.

The expression control sequences can also be those responsive to substances that modulate cell-surface receptors or that modulate intracellular receptors. To determine whether a substance or mixture of substances activates extracellular or intracellular receptors or other cellular responses, cells containing a beta-lactamase enzyme controlled by a desired promoter/enhancer element can be incubated with at least one test substance. A compound of this invention is then added, and after a period of time has passed, the fluorescence emission of the cleaved substrate is measured. This result is compared to fluorescent emissions from control samples that have had no drug treatment and, when feasible, control samples with a known inhibitor and a known activator. The effect of any active drugs may then be determined using the ratio of the fluorescence signal found in test wells to the signals found in wells with no drug treatment.

Assays are performed in wells in a microtiter plate containing 96 or more wells, or in an assay system with no compartments, such as a gel matrix or moist membrane environment. Detection can be performed for example by microtiter plate fluorimeters, e.g., Millipore Cytofluor®, or imaging devices capable of analyzing one or more wells or one or more assay points in a certain surface area (e.g., as supplied by Astro-med West Warwick, R. I.). Furthermore, the fluorescent signal from the cleaved substrate can be detected in single cells, which allows assay miniaturization and an increased number of tests per surface area. Miniaturized assays also further increase the throughput of an imaging detection system because there are more samples within the imaging field.

The assay systems of the present invention may further provide an advantageous and rapid method of isolation and clonal selection of stably transfected cell lines containing reporter genes and having the desired properties which the transfection was intended to confer, e.g., fluorescent signal response after activation of a transfected receptor from a high proportion of isolated cells. Current procedures for clonal selection of satisfactorily transfected, genetically engineered cells from the population initial transfected with the vectors of interest, are done mainly by manual means and involve several rounds of microscopic analyses, selecting the visually preferred clone, isolation of the clone by manual pipetting stages and prolonged cellular cultivations. This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system may be maintained within living and viable cells. Thus, one may rapidly select, from the population of initially transfected cells, those few living cells with the best fluorescent signal using automated instruments such as a fluorescent-activated cell sorter, e.g. the Becton Dickinson FACS Vantage. The selected cells may then be collected for cultivation and propagation to produce a clonal cell line with the desired properties for assays and drug screening.

In addition, the presence (for example, in human serum, pus, urine, or other fluid, sample, or tissue) of bacteria resistant to beta-lactam antibiotics may be readily detected by using the substrates of this invention. Only in the presence of an active beta-lactamase enzyme is there a fluorescence spectrum that is characteristic of the cleaved compound.

Some of the aspects and embodiments invention may be better understood with reference to the accompanying examples, which are intended for purposes of illustration only and should not be construed as in any sense limiting the scope of the invention as defined in the claims appended hereto.

EXAMPLES

Examples 1, 2 and 3 describe the synthesis of compounds having the general formula 1:

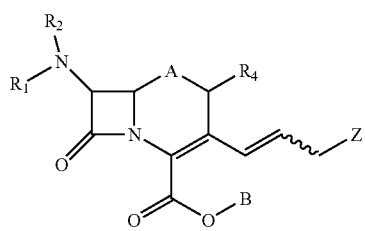

Formula 1 in which Z includes a fluorophore or chromophore and includes a group that may link to the lactam-containing group (such as, for example, a phenolic group, an amine, a thiophenol, thiol or thioether, or other group); $R_1$ and $R_2$ are selected from H, aliphatic, alkyl, and acyl (including, for example, a benzyl, 2-thienylmethyl, or cyanomethyl group, or a quencher); $R_4$ is any substitution that does not compromise the efficiency of hydrolysis of the compound by beta-lactamase (including, for example, H and lower alkyl); B is selected from the group consisting of H, physiologically acceptable salts or metal, ester groups, ammonium cations, —$CHR_5OCO(CH_2)_nCH_3$, —$CHR_5OCOC(CH_3)_3$, acylthiomethyl, acyloxy-alpha-benz, deltabutyrolactonyl, methoxycarbonyloxymethyl, phenyl, methylsulphinylmethyl, beta-morpholinoethyl, dialkylaminoethyl, and dialkylaminocarbonyloxymethyl, in which $R_5$ is selected from the group consisting of H and lower alkyl; n is an integer between 0 and 10, inclusive, and is preferably an integer between 1 and 5, inclusive; A is selected from the group consisting of S, O, SO, $SO_2$ and $CH_2$.

Example 1

Synthesis and Characterization of Compounds CC1 and CC2

Compounds CC1 and CC2 were synthesized according to Scheme 1:

Scheme 1

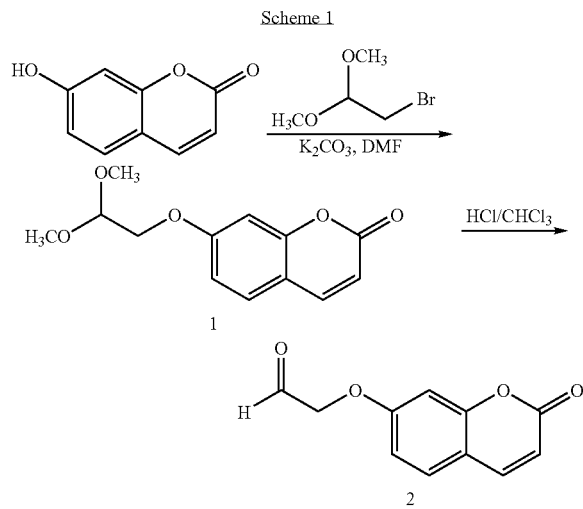

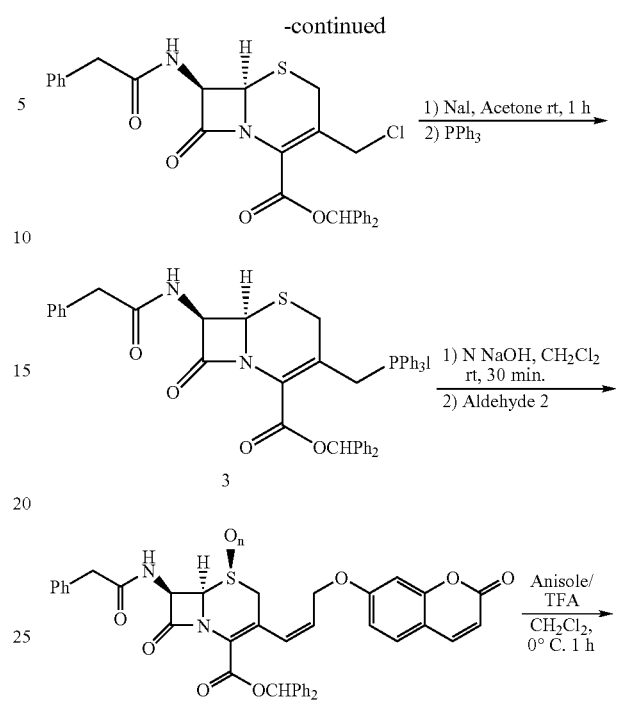

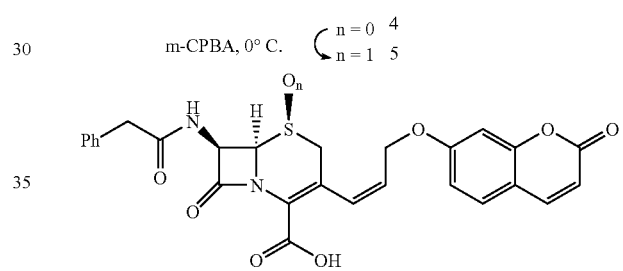

CC1 n = 0  CC2 n = 1

Preparation of 1: A mixture of 7-hydroxycoumarin (0.812 g, 5.0 mmol), bromoacetaldehyde dimethyl ketal (3.380 g, 20.0 mmol), and potassium carbonate (0.829 g, 6.0 mmol) in 15 mL of DMF was heated to 115° C. for 12 hours. After cooling to room temperature, the reaction mixture was diluted with 150 mL of ethyl acetate, washed with 1 M sodium hydroxide (25 mL×3) and brine (25 mL×3), and dried over anhydrous magnesium sulfate. After evaporation, the residue was purified by flash chromatography on silica gel (eluent: ethyl acetate/hexane=1/1) to afford 1.019 g (82%) of title compound: $^1$H NMR (400 MHz, $CDCl_3$) δ 7.63 (d, J=9.5 Hz, 1 H), 7.3 7 (d, J=8.6 Hz, 1 H), 6.8 7 (dd, J=8.6 and 2.4 Hz, 1 H), 6.8 3 (d, J=2.4 Hz, 1 H), 6.25 (d, J=9.5 Hz, 1 H), 4.73 t, J=5.1 Hz, 1 H), 4.05 (d, J=5.1 Hz, 2 H), 3.47 (s, 6 H).

Preparation of 2: To a solution of 1 (0.200 g, 0.8 mmol) in 12 mL of chloroform was added dropwise 4 mL of concentrated HCl with cooling (ice bath). The resultant mixture was stirred for additional 30 minutes at the same temperature, and then diluted with 50 mL of dichloromethane. The organic phase was washed with brine (25 mL×3), dried over anhydrous magnesium sulfate. After evaporation, the residue was purified by flash chromatography on silica gel (eluent: ethyl acetate/hexane=1/1 to ethyl acetate) to afford 0.104 g (63%) of title compound: $^1$H NMR (400 MHz, $CDCl_3$) δ 9.87 (d, J=0.8 Hz, 1 H), 7.65 (d, J=9.5 Hz, 1 H), 7.42 (d, J=8.6 Hz, 1

H), 6.89 (dd, J=8.6 and 2.5 Hz, 1 H), 6.80 (d, J=2.5 Hz, 1 H), 6.30 (d, J=9.5 Hz, 1 H), 4.67 (d, J=0.8 Hz, 2 H.

Preparation of 3: A mixture of 7-phenylacetamido-3-chloromethyl cephalosporanic acid benzhydryl ester (0.532 g, 1.0 mmol; "GCLE" Otsuka Chemical Co., Ltd.) and sodium iodide (0.750 g, 5.0 mmol) in 6 mL of acetone was stirred for 1 hour at ambient temperature. The reaction mixture was concentrated under reduced pressure and diluted with 5 mL of water. The suspension was extracted with 25 mL of ethyl acetate, and the organic phase was washed with 10% sodium thiosulfate (5 mL), water (5 mL), brine (5 mL) and dried over anhydrous magnesium sulfate. The volume was then reduced to about 10 mL by evaporation, and triphenylphosphine (0.315 g, 1.2 mmol) was added in one portion. The mixture was stirred for 12 hours, and the resultant precipitates were collected by filtration, washed with tiny amount of ethyl acetate and dried to afford 0.715 g (81%) of desired ylide salt.

Preparation of 4: Ylide salt 3 (0.398 g, 0.45 mmol) was dissolved in 12 mL of dichloromethane. The resultant solution was treated with 4 mL of 1 M sodium hydroxide for 30 minutes at room temperature. Then the organic phase was separated and dried over anhydrous magnesium sulfate. After filtration, the filtrate was added to the flask containing aldehyde (0.062 g, 0.3 mmol), and the mixture was stirred at room temperature over night. After evaporation, the residue was purified by flash chromatography on silica gel (eluent: ethyl acetate/hexane=1/2) to afford 0.057 g (28%) of title compound: $^1$H NMR (400 MHz, CDCl$_3$) δ 7.59 (d, J=9.5 Hz, 1 H), 7.42-7.18 (m 16 H), 6.92 (s, 1 H), 6.65 (dd, J=8.5 and 2.4 Hz, 1 H), 6.62 (d, J=2.4 Hz, 1 H), 6.32-6.15 (m, 3 H), 5.86 (dd, J=8.9 and 4.9 Hz, 1 H), 5.73-5.65 (m, 1 H), 4.99 (d, J=4.9 Hz, 1 H), 4.34 (ddd, J=12.8, 7.1 and 1.2 Hz, 1 H), 4.05 (ddd, J=12.8, 5.4 and 1.5 Hz, 1 H), 3.68 (d, J=16.0 Hz, 1 H), 3.62 (d, J=16.0 Hz, 1 H), 3.45 (d, J=18.3 Hz, 1 H), 3.26 (d, J=18.3 Hz, 1 H); FAB-MS(m/z): calculated 684.19 (C$_{40}$H$_{32}$N$_2$O$_7$S), found: 685.12 (M+H$^+$).

Preparation of CC1: To a solution of 4 (14.5 mg, 0.02 mmol)) in 1.5 mL of dry dichloromethane was added anisole (75 μL) and trifluoroacetic acid (200 μL) with cooling (ice bath). The mixture was stirred for 1 hour at the same temperature, then the solvent was evaporated under reduced pressure and the residue was washed with ether (1 mL×3) to afford 7.8 mg (71%) of the desired product as a solid: $^1$H NMR (400 MHz, d$_6$-DMSO) δ 13.52 (br, 1 H), 9.08 (d, J=8.1 Hz, 1 H), 7.96 (d, J=9.4 Hz, 1 H), 7.60 (d, J=8.5 Hz, 1 H), 7.35-7.15 (m, 5 H), 7.00-6.88 (in, 2 H), 6.46 (d, J=11.5 Hz, 1 H), 6.26 (d, J=9.5 Hz, 1 H), 5.85-5.70 (m, 1 H), 5.70-5.68 (m, 1 H), 5.11 (d, J=4.7 Hz, 1 H), 4.77 (dd, J=12.9 and 6.8 Hz, 1 H), 4.64 (dd, J=12.9 and 5.4 Hz, 1 H), 3.72 (d, J=17.8 Hz, 1 H), 3.55 (d, J=17.8 Hz, 1 H), 3.54 (d, J=13.9 Hz, 1 H), 3.46 (d, J=13.9 Hz, 1 H); FAB-MS(m/z): calculated 518.1 (C$_{27}$H$_{22}$N$_2$O$_7$S), found: 519.1 (M+H$^+$).

Preparation of 5: To a solution of 4 (28.3 mg, 0.04 mmol) in 1 mL of dry dichloromethane was added a solution of m-CPBA (10.2 mg, 68%, 0.04 mmol) in 0.5 mL of dichloromethane with cooling (ice bath). After 20 minutes, the TLC indicated the disappearance of all starting material. The mixture was diluted with 25 mL of dichloromethane, washed with 1 M sodium bicarbonate (6 mL×2) and brine (6 mL×2), dried over anhydrous magnesium sulfate. After evaporation, 27.0 mg (93%) of crude product was afforded. This crude product was used for next transformation without further purification: $^1$H NMR (400 MHz, d$_6$-DMSO) δ 8.48 (d, J=8.2 Hz, 1 H), 7.93 (d, J=9.5 Hz, 1 H), 7.55 (d, J=8.5 Hz, 1 H), 7.46 (d, J=7.5 Hz, 2 H), 7.36 (d, J=7.5 Hz, 2 H), 7.32-7.15 (m, 11 H), 6.91 (s, 1 H), 6.81 (d, J 2.3 Hz, 1 H), 6.79 (dd, J=8.5 and 2.3 Hz, 1 H), 6.35 (d, J=11.7 Hz, 1 H), 6.26 (d, J=9.5 Hz, 1 H), 5.86 (dd, J=8.2 and 4.4 Hz, 1 H), 5.73-5.65 (m, 1 H), 4.94 (d, J=4.4 Hz, 1 H), 4.58 (dd, J=13.6 and 6.8 Hz, 1 H), 4.31 (dd, J=13.6 and 4.1 Hz, 1 H), 3.97 (d, J=18.2 Hz, 1 H), 3.67 (d, J=18.2 Hz, 1 H), 3.46 (d, J=14.0 Hz, 1 H), 3.53 (d, J=14.0 Hz, 1 H); FAB-MS(m/z): calculated 700.19 (C$_{40}$H$_{32}$N$_2$O$_8$S), found: 701.13 (M+H$^+$).

Preparation of CC2: To a solution of 5 (27.0 mg, 0.04 mmol)) in 3 mL of dry dichloromethane was added anisole (70 μL) and trifluoroacetic acid (200 μL) with cooling (ice bath). The mixture was stirred for 1 hour at the same temperature, then the solvent was evaporated under reduced pressure and the residue was washed with ether (1 mL×3) to afford 16.7 mg (81%) of the desired product as a solid: $^1$H NMR (400 MHz, d$_6$-DMSO) δ 13.66 (br, 1 H), 8.42 (d, J=8.1 Hz, 1 H), 7.96 (d, J=9.4 Hz, 1 H), 7.60 (d, J=8.6 Hz, 1 H), 7.35-7.15 (m, 5 H), 6.93 (s, 1 H). 6.90 (d, J=8.6 Hz, 1 H), 6.49 (d, J 11.8 Hz, 1 H), 6.26 (d, J=9.4 Hz, 1 H), 5.85-5.70 (m, 2 H), 4.87 (d, J=3.7 Hz, 1 H), 4.77 (dd, J=13.2 and 5.7 Hz, 1 H), 4.62 (dd, J=13.2 and 4.8 Hz, 1 H), 3.95 (d, J=18.1 Hz, 1 H), 3.67 (d, J=18.1 Hz, 1 H), 3.66 (d, J=14.0 Hz, 1 H), 3.51 (d, J 14.0 Hz, 1 H FAB-MS(m/z): calculated 534.11 (C$_{27}$H$_{22}$N$_2$O$_8$S), found: 535.18 (M+H$^+$).

Example 2

Synthesis and Characterization of CR2 and CR2/AM

CR2 and CR2/AM were synthesized in similar procedures to that of CC2 with some modifications (Scheme 2).

Scheme 2

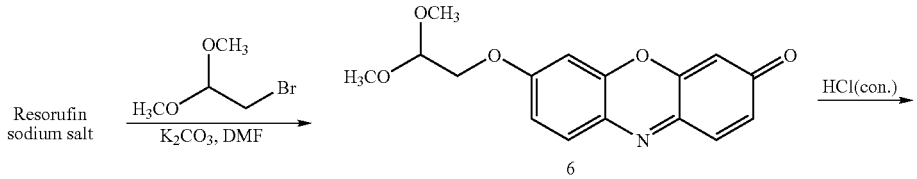

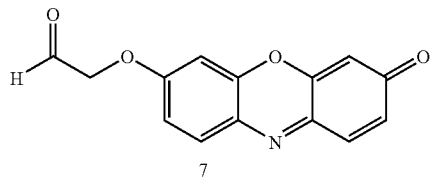

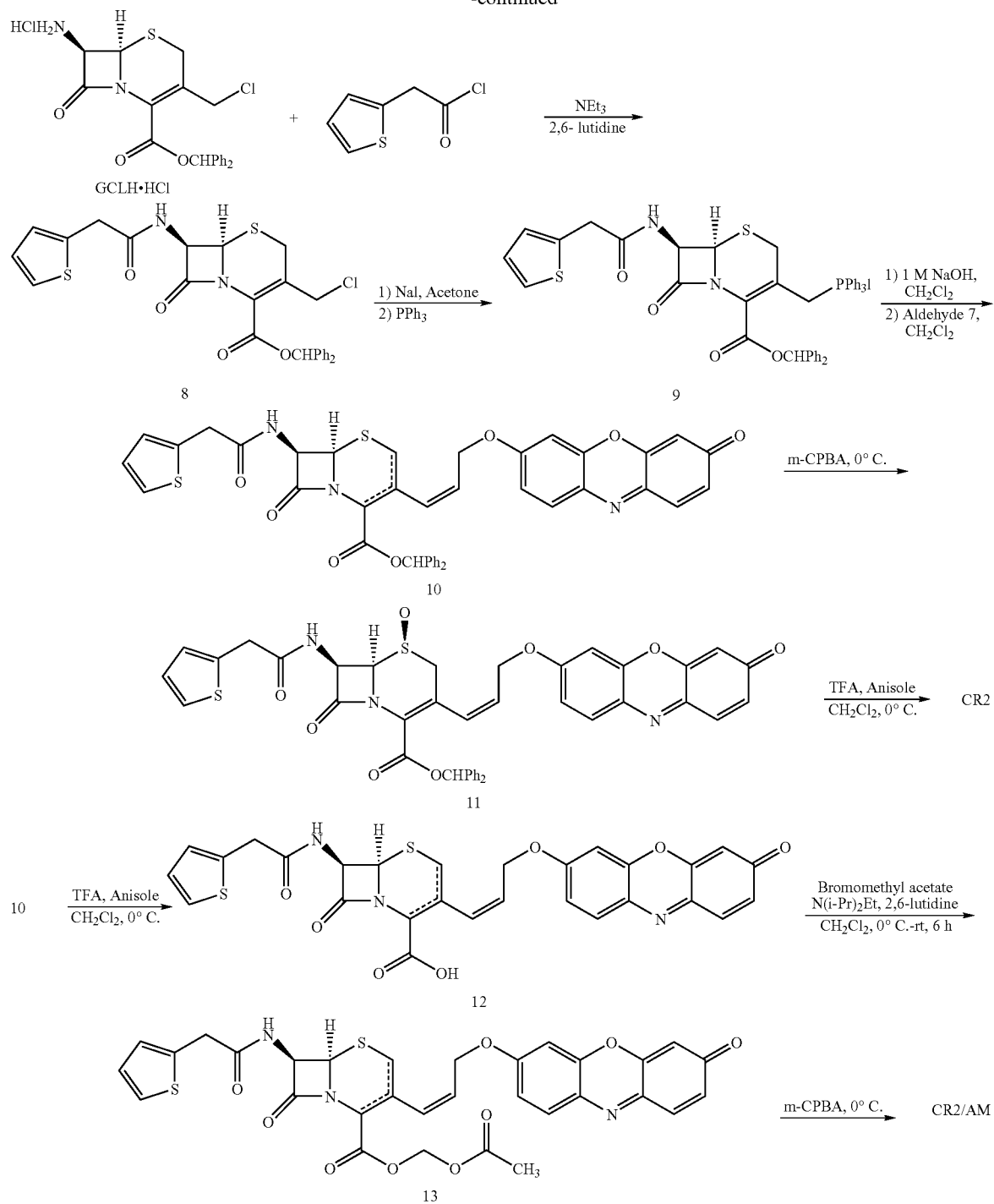

Preparation of 6: A mixture of resorufin sodium salt (0.233 g, 1.0 mmol), bromoacetaldehyde dimethyl ketal (0.5 mL, 4.1 mmol), and potassium carbonate (0.208 g, 1.5 mmol) in 10 mL of DMF was heated to 115-120° C. for 48 hours. After being cooled to room temperature, the reaction mixture was diluted with 100 mL of ethyl acetate, washed with 1 M sodium hydroxide (10 mL×4) and brine (15 mL×2), dried over anhydrous magnesium sulfate. After evaporation, the residue was purified by flash chromatography on silica gel (eluent: dichloromethane/methanol) to afford 0.105 g (35%) of title compound: $^1$H NMR (400 MHz, CDCl$_3$) δ 7.64 (d, J=8.9 Hz, 1 H), 7.35 (d, J=9.8 Hz, 1 H), 6.90 (dd, J=8.9 and 2.6 Hz, 1 H), 6.80-6.72 (m, 2 H), 6.25 (d, J=2.0 Hz, 1 H), 4.68 (t, J=5.1 Hz, 1 H), 4.03 (d, J=5.1 Hz, 2 H), 3.42 (s, 6 H).

Preparation of 7: To a solution of 6 (0.151 g, 0.5 mmol) in 15 mL of chloroform was added in dropwise 3 mL of concentrated HCl with cooling (ice bath), the resultant dark mixture was stirred for 12 minutes at the same temperature, then diluted with 120 mL of dichloromethane. The organic phase was washed with brine (20 mL×2), dried over anhydrous magnesium sulfate. After evaporation, 0.044 g (34%) of crude aldehyde was produced. This crude aldehyde was used for next step without further purification.

Preparation of 8: A mixture of GCLH HCl (1.448 g, 3.2 mmol), triethylamine (420 μL, 3.0 mmol), 2,6-lutidine (700 μL, 6.2 mmol) and thiophenylacetyl chloride (550 μL, 4.5 mmol) in 20 mL of anhydrous $CH_3CN$ was stirred at 0° C. After being warmed to room temperature over 4 hours, the reaction mixture was diluted with 150 mL of ethyl acetate, washed with saturated sodium bicarbonate (25 mL×2) and brine (25 mL×2), dried over anhydrous magnesium sulfate. After evaporation, the residue was purified by flash chromatography on silica gel (eluent: ethyl acetate/hexanes) to afford 1.550 g (90%) of title compound: $^1$H NMR (400 MHz, $CDCl_3$) δ 7.45-7.25 (m, 11 H), 7.05-6.94 (m, 3 H), 6.37 (d, J=9.1 Hz, 1 H), 5.86 (dd, J=9.1 and 5.0 Hz, 1 H), 4.98 (d, J=5.0 Hz, 1 H) 4.39 (d, J=11.8 Hz, 1 H), 4.35 (d, J=11.8 Hz, 1 H), 3.85 (s, 2 H), 3.59 (d, J=18.3 Hz, 1 H), 3.44 (d, J=18.3 Hz, 1 H).

Preparation of ylide salt 9: A mixture of 8 (1.43 7 g, 2.6 8 mmol) and sodium iodide (2.00 8 g, 13.4 mmol) in 16 mL of acetone was stirred for 1 hour at ambient temperature. The reaction mixture was concentrated under reduced pressure, extracted with 70 mL of ethyl acetate, and the organic phase was washed with 10% sodium thiosulfate (15 mL×2), brine (15 mL×2), and dried over anhydrous magnesium sulfate. After reducing the volume to about 30 mL by evaporation, triphenylphosphine (0.877 g, 3.35 mmol) was added in one portion and the mixture was stirred overnight. The resultant precipitates were collected by filtration, washed with ethyl acetate (6 mL×2) and dried to afford 1.950 g (82%) of desired ylide salt.

Preparation of 10: Ylide salt 9 (0.305 g, 0.34 mmol) was dissolved in 12 mL of dichloromethane, the resultant solution was treated with 4 mL of 1 M sodium hydroxide for 30 minutes at room temperature. Then the organic phase was separated and dried over anhydrous magnesium sulfate, filtered, the filtration was added to the flask containing aldehyde 7, and the mixture was stirred at room temperature overnight. After evaporation, the residue was purified by flash chromatography on silica gel (eluent: acetonitrile/benzene) to afford 0.044 g (35%) of title compound as an inseparable A2 and A3 mixture.

Preparation of 11: To a solution of ester 10 (21.0 mg, 0.028 mmol) in 5 mL of anhydrous dichloromethane, was added a solution of m-CPBA (7.1 mg, 68% purity, 0.028 mmol) in 1 mL of dichloromethane with cooling (ice bath), after 40 minutes, the TLC indicated all starting material disappeared. The mixture was diluted with 50 mL of dichloromethane, washed with 1 M sodium bicarbonate (8 mL×2) and brine (8 mL×2), dried over anhydrous magnesium sulfate. After evaporation, 16.2 mg (75%) of crude product was afforded. This crude product was used for next transformation without further purification: $^1$H NMR (400 MHz, $d_6$-DMSO) –δ 8.51 (d,J=8.3Hz, 1 H), 7.69 (d,J=9.5 Hz, 1 H), 7.60-7.18 (m, 12 H), 6.95-6.85 (m, 5 H), 6.76 (dd, J=9.8 and 2.2 Hz, 1 H), 6.39 (d, J=11.7 Hz, 1 H), 6.24 (d, J=2.2 Hz, 1 H), 5.90 (dd, J=8.3 and 4.2 Hz, 1 Hz, 1 H), 5.75-5.65 (m, 1 H), 4.96 (d, J=4.2 Hz, 1 H), 4.64 (dd, J=13.2 and 6.3 Hz, 1 H), 4.39 (dd, J=13.2 and 4.0 Hz, 1 H), 3.99 (d, J=18.3 Hz, 1 H), 3.88 (d, J=15.3 Hz, 1 H), 3.79 (d, J 15.3 Hz, 1 H), 3.68 (d, J=18.3 Hz, 1 H); FAB-MS (m/z): calculated 757.16 ($C_{41}H_{31}N_3O_8S_2$), found: 758.32 (M+H$^+$).

Preparation of CR2: To a solution of ester 11 (12.0 mg, 0.016 mmol) in 1 mL of anhydrous dichloromethane, was added anisole (50 μL) and trifluoroacetic acid (150 μL) with cooling (ice bath), the mixture was stirred for 1 hour at the same temperature, then the solvent was evaporated under reduced pressure and the residue was washed with ether (1 mL×3) to afford 5.5 mg (59%) of the desired product as a solid: $^1$H NMR (400 MHz, d6-DMSO) δ 8.46 (d, J=8.3 Hz, 1 H), 7.75 (d, J=8.8 Hz, 1 H), 7.50 (d, J=9.8 Hz, 1 H), 7.36-7.32 (m, 1 H), 7.12-7.08 (m, 1 H), 7.00 (dd, J=8.8 and 2.6 Hz, 1 H), 6.95-6.88 (m, 2 H), 6.76 (dd, J=9.8 and 2.0 Hz, 1 H), 6.50 (d, J=12.0 Hz, 1 H), 6.25 (d, J=2.0 Hz, 1 H), 5.85-5.75 (m, 2 H), 4.90 (d, J=3.6 Hz, 1 H), 4.83 (dd, J=13.5 and 5.4 Hz, 1 Hz, 1 H), 4.69 (dd, J=13.5 and 4.2 Hz, 1 H), 3.97 (d, J=18.1 Hz, 1 H), 3.88 (d, J=15.4 Hz, 1 H), 3.78 (d, J=15.4 Hz, 1 H), 3.6 9 (d, J=18.1 Hz, 1 H).

Preparation of CR2/AM: To a solution of ester 10 (35.5 mg, 0.048 mmol) in 2 mL of dry dichloromethane, was added anisole (100 μL) and trifluoroacetic acid (300 μL) with cooling (ice bath), the mixture was stirred for 1 hour at the same temperature, then the solvent was evaporated under reduced pressure and the residue was washed with ether (1 mL×3) to afford 26.2 mg (95%) of the desired product 12 as a solid. Compound 12 (24.7 mg, 0.04 mmol) was suspended in 4 mL of anhydrous dichloromethane and cooled to 0° C., then was added sequentially bromomethyl acetate (32 μL, 0.20 mmol), 2,6-lutidine (50 μL, 0.36 mmol) and diisopropylethylamine (8 μL, 0.04 mmol). The mixture was warmed to room temperature over 6 hours. After the removal of all the solvents, the residue was purified by flash chromatography on silica gel (eluent: dichloromethane/methanol) to afford 6.5 mg (23%) of the desired product 13 as a solid.

To a solution of 13 (6.5 mg, 0.01 mmol) in 1.5 mL of anhydrous dichloromethane, was added a solution of m-CPBA (2.6 mg, 68% purity, 0.01 mmol) in 0.5 mL of dichloromethane with cooling (ice bath). After 30 minutes, the TLC indicated all starting material had disappeared. The mixture was diluted with 60 mL of dichloromethane, washed with saturated sodium bicarbonate (6 mL) and brine (10 mL×2), dried over anhydrous magnesium sulfate. After evaporation, the desired CR2/AM was afforded as a solid in 3.6 mg (54%): $^1$H NMR (400 MHz, d6-DMSO) δ 8.47 (d, J=8.1 Hz, 1 H), 7.75 (d, J=8.8 Hz, 1 H), 7.50 (d, J=9. 8 Hz, 1 H), 7.36-7.32 (m, 1 H), 7.06-7.02 (m, 1 H), 6.99 (dd, J=8.8 and 2.4 Hz, 1 H), 6.96-6.8 5 (m, 2 H), 6.75 (dd, J=9.8 and 2.1 Hz, 1 H), 6.41 (d, J=11.2 Hz, 1 H), 6.25 (d, J=2.1 Hz, 1 H), 5.90-5.82 (m, 2 H), 5.81 (d, J=6.2 Hz, 1 H), 5.76 (d, J=6.2 Hz, 1 H), 4.92 (d, J=3.4 Hz, 1 H), 4.78 (dd, J 13.1 and 6.4 Hz, 1 H), 4.67 (dd, J=13.1 and 5.4 Hz, 1 H), 4.02 (d, J=17.9 Hz, 1 H), 3.88 (d, J=15.4 Hz, 1 H), 3.77 (d, J=15.4 Hz, 1 H), 3.67 (d, J=17.9 Hz, 1 H), 2.03 (s, 3 H); FAB-MS(m/z): calculated 663.10 ($C_{31}H_{25}N_3O_{10}S_2$) found: 663.65 (M+H$^+$).

Enzyme kinetics. The kinetic experiment was carried out at 25° C. in 0.1 M of phosphate-buffered saline (PBS) at pH 7.1. The fluorescence measurements were taken on a GENios microplate reader (TECAN, Research Triangle Park, N.C.). To a series of different concentrations of substrate CC1 (200, 160, 140, 100, 75, 60, 50, 30 μM) were added a solution of 50 nM TEM-1 β-lactamase in a 96-well clear bottom plate. PBS was added to adjust the final volume to 100 μL. Then the plate was transferred to a GENios microplate reader for fluorescence measurement. The rate of increase in fluorescence intensity at 465 nm was used to determine the kinetic properties of enzyme hydrolysis. The values of the kinetic parameters ($K_m$ and $K_{cat}$) were determined from the double-reciprocal plot of the hydrolysis rate versus substrate concentration (Lineweaver-Burk plot).

Quantitation of β-lactamase in the cell lysates. Both cmv-bla and wild-type Jurkat cells were suspended in the phosphate buffer (pH 7.0) at a density of 5×10$^5$ cell/mL. They were mixed at various ratio (0, 0.5, 1, 5, 10, 25, 50, 75, 100% of cmv-bla Jurkats) with the total cell number maintained at 5×10$^5$. The cell mixtures were centrifuged at 12500×g for 5 min at 4° C. to harvest the cell. The cells were resuspended in 50 μl PB buffer and were lysed by shock freezing. The samples were exposed to isopropyl alcohol with dry ice until the content froze and then warmed to 30° C. After three freeze/thaw cycles, the cell debris was spun into pellet by centrifugation at 12500×g for 2 min at 4° C. Then the lysate (45 μl) was placed into a well of clear-bottom microtiter plate and 5 μl of 1 mM substrate CC1 was added for the Bla hydrolysis rate measurement. Wells with 45 μl PB buffer and 5 μl of 1 mM substrate CC1 serve as the baseline control. The measurement readings were taken initially at 3 min intervals for the first hour and then hourly for another 5 hours to allow assessments of very low enzyme concentrations.

Example 3

Synthesis, Characterization, and Use of Novel Fluorogenic Substrates

More fluorogenic substrates would expand the usefulness of Bla as a biosensor. Here we report a new class of small fluorogenic substrates that work by releasing a phenolate from a vinylogous cephalosporin.

Cleavage of the β-lactam ring of a cephalosporin creates a free amino group, which triggers spontaneous elimination of any leaving group previously attached to the 3' position (Page, M. I. Adv. Phys. Org. Chem. 1987, 23, 165-270). Umbelliferone is a widely used fluorophore with maximal excitation at 360 nm and emission at 460 nm. When its 7-hydroxy group is alkylated, the compound becomes essentially nonfluorescent. We thus designed and synthesized a β-lactam called CC1 in which the 3' position of the cephalosporin is linked to the 7-hydroxy group of umbelliferone through an allylic ether bond (Scheme 1). The 3'-vinyl cephems have been reported as potential antibiotics, but little was known about their kinetics as β-lactamase substrates. With the 7-hydroxy group of umbelliferone alkylated, CC1 should be essentially non-fluorescent, and if Bla hydrolysis leads to spontaneous release of umbelliferone, in this case through an extended conjugation system, fluorescent signals will be produced (FIG. 11A). The complete synthesis of CC1 is as described in Scheme 1 of Example 4. The Wittig coupling reaction exclusively afforded the Z-isomer, as shown by its $^1$H NMR.

We first examined the emission spectrum of CC1 before and after the Bla treatment, and observed a 153-fold increase in the intensity at the wavelength of 460 run upon complete hydrolysis of CC1 (FIG. 11B). This result validates that Bla cleaves CC1 and releases the fluorophore umbelliferone. The increase in the fluorescent emission at 460 nm is considerably larger than the 20-fold enhancement of CCF2 at similar wavelengths and affords a convenient means to measure the Bla activity. In the phosphate-buffered saline (PBS) at pH 7.1, CC1 is hydrolyzed by TEM-1 Bla with catalytic constant $(k_{cat})=52\pm1$ s$^{-1}$ and Michaelis constant $(K_m)=70\pm7$ μM (values were obtained from weighted least squares fit of a double-reciprocal plot of the hydrolysis rate versus CC1 concentrations); its catalytic efficiency $(k_{cat}/K_m)$ is 7.4×10$^5$ M$^{-1}$ s$^{-1}$. The spontaneous hydrolysis rate constant of CC1 in the PBS is ~1.3×110$^{-6}$ s$^{-1}$, and the enzymatic acceleration is ~4×10$^7$ fold.

FIG. 11A shows that hydrolysis of CC1 by β-lactamase releases the fluorophore umbelliferone. FIG. 11B shows the emission spectrum of CC1 (10 nM in PBS) before (dash dot line) and after (solid line) treatment of β-lactamase (excitation at 400 nm). FIG. 12 illustrates the linear nature of the dependence of the CC1 hydrolysis rate on the β-lactamase concentration. Wild-type and CMV-bla Jurkat cells were mixed at different ratios (with the percentage of CMV-bla Jurkat cells from 0, 0.5, 1, 5, 10, 25, 50, 75, to 100%), lysed and diluted for CC1 assay with excitation at 365/42 nm and emission at 465/35 nm.

Compared to CCF2 ($k_{cat}$=29 s$^{-1}$ and Km=23 μM) (Zlokarnick et al., Science 279:84-88 (1998)), CC1 has a 3-fold lower affinity for Bla, but its $k_{cat}$ is nearly twice as fast. Since CC1 itself is non-fluorescent, a higher concentration can be used to obtain a faster hydrolysis rate. The stability of CC1 in the absence of Bla can be further improved by oxidation of the sulfide in the six-member ring to sulfoxide CC2, which resulted in a 4-fold decrease in the spontaneous hydrolysis rate (~2.6×10$^{-7}$ s$^{-1}$). CC2 remains as a substrate with slightly less catalytic efficiency ($k_{cat}$=10 s$^{-1}$ and Km=0.35 mM). CC2 may be useful for experiments where a longer incubation is needed.

The ability of CC1 in detecting Bla activity was tested by measuring the percentage of Bla-expressed cells in a cell mixture. Wild-type Jurkat cells do not express any Bla, and a clonal Jurkat cell line constitutively transfected with Bla gene under the cytomegalovirus (CMV) promoter control (CMV-bla Jurkat cells) expresses approximately 1.5×10$^4$ 04 Bla/cell. (Zlokarnik, G. Methods in Enzymology 2000, 326, 221-241). Two cell lines were mixed at different ratios, and the cell lysates were analyzed with CC1 for the Bla activity. A plot of the apparent hydrolysis rate versus the percentage of CMV-bla Jurkat cells reveals a linear relationship (FIG. 12). This assay can reliably detect 0.5% CMV-bla Jurkat cells in the background of wild type cells, which corresponds to approximately 500 fM of Bla.

The importance of the inserted double bond is further exemplified in making a red fluorescent substrate, which is preferred due to a longer excitation and emission wavelength. Resorufin fluoresces at 585 nm when exited at 550 nm, and a structure with resorufin directly linked to the 3'-position of cephalosporin has been made but found to spontaneously hydrolyze rapidly in water. However, an analog of CC2 with umbelliferone replaced by resorufin (CR2) is stable in PBS buffer with a half life of 182 hrs. CR2 displays a 42-fold increase in the fluorescence intensity upon the hydrolysis by Bla with the catalytic parameters ($k_{cat}$=17±3 s$^{-1}$ and $K_m$=114±12 μM. A membrane-permeable acetoxymethyl ester of CR2 (CR2/AM) was able to image the Bla activity in Bla-stably-transfected C6 glioma cells (FIGS. 13A and 13B).

Figure 13A:
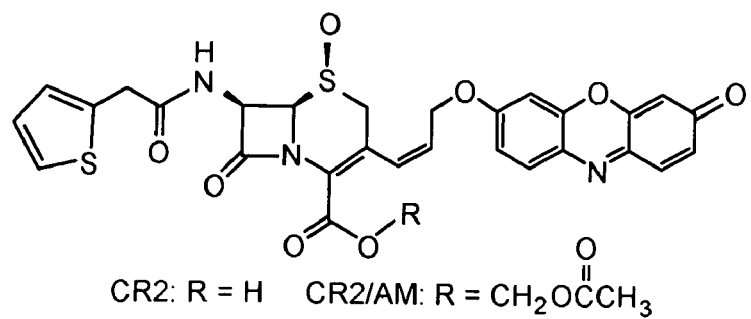
FIG. 13A shows the structures of CR2 and CR2/AM.
Figure 13B:
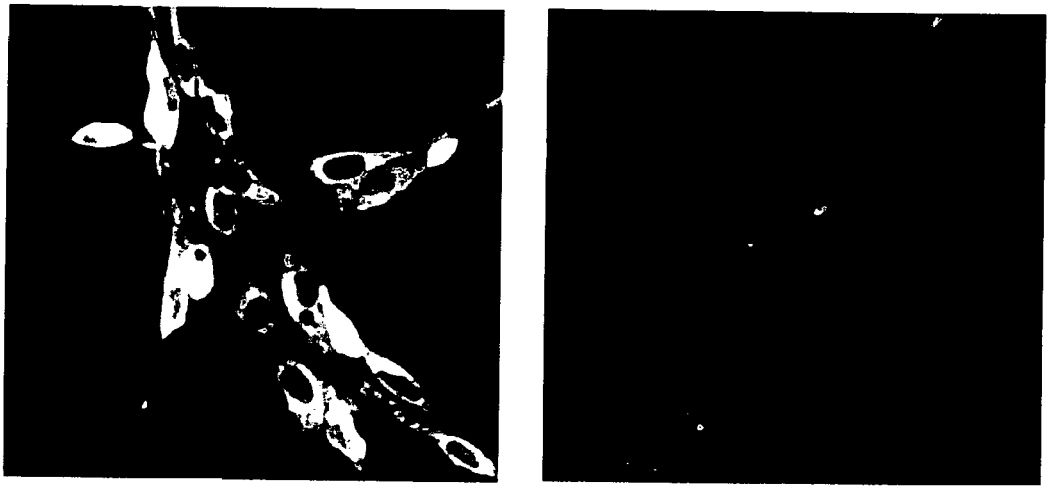
FIG. 13B shows fluorescence images of wild type (right) and Bla-stably-transfected (left) C6 glioma cells loaded with CR2/AM.

FIG. 13A illustrates the structures of CR2 and CR2/AM. FIG. 13B presents fluorescence images (40×magnification) of wild type (right) and Bla-stably-transfected (left) C6 glioma cells loaded with CR2/AM in Hank's Balanced Salts Solution for 25 min at room temperature. The excitation filter was set at 540/25 (540 nm peak with a width of 25 nm around the peak). The emission filter was set at 635/55.

Figure 14:
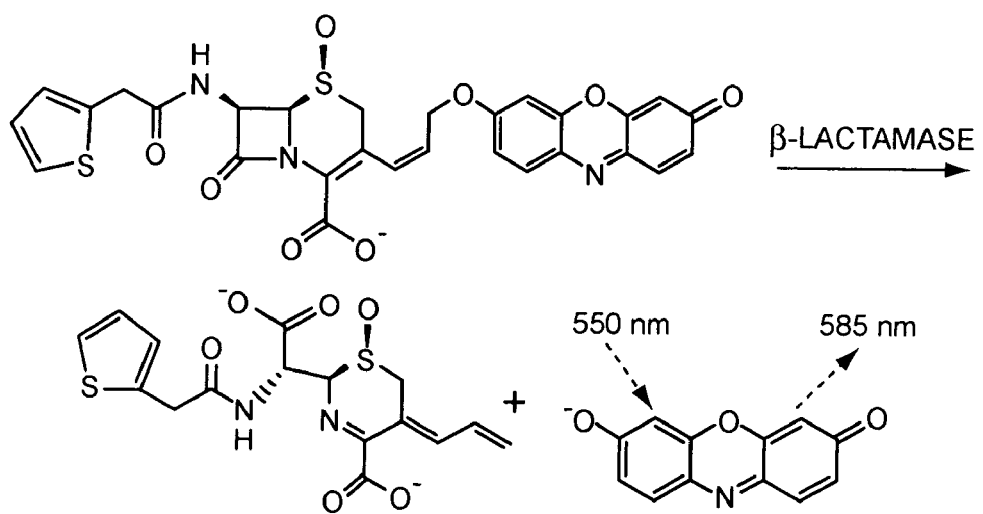
FIG. 14 shows a scheme for cleavage of CR2/AM by beta-lactamase to release a fluorophore which, upon excitation by energy at wavelengths of about 550 nm fluoresces at wavelengths of about 585 nm.

FIG. 14 shows a scheme for cleavage of CR2/AM by beta-lactamase to release a fluorophore which, upon excitation by energy at wavelengths of about 550 nm fluoresces at wavelengths of about 585 nm. The Figures illustrate examples of how the compounds disclosed herein provide a new class of small non-fluorogenic substrates that become brightly fluorescent after the B-lactamase hydrolysis with up to 153-fold enhancement in the fluorescence intensity. Less the 500 fM of B-lactamase in cell lysates can be readily detected with the novel compounds and B-lactamase expression in living cells can be imaged with a red fluorescence derivative. These new fluorogenic substrates should find uses in clinical diagnostics and facilitate the applications of B-lactamase as a biosensor.

This application describes a design of a new class of fluorogenic substrates of β-lactamase and characterization of its enzymatic kinetics, and demonstrates its applicability in detecting β-lactamase activity in biological samples with the determination of β-lactamase in cell mixtures and living cells. These new fluorogenic substrates are easy to make, simple to use, have high sensitivity for detecting β-lactamase activity, and should facilitate applications with β-lactamase as a biosensor. The design reported here is not limited to umbelliferone and resorufin, and could be extended to other molecules containing phenolic leaving groups. The design reported here may serve as a general strategy to create a wide variety of fluorogenic, chromogenic, and lumogenic substrates for β-lactamase.

The present invention provides novel substrates for beta-lactamase, beta-lactamases and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are hereby incorporated herein by reference in their entirety for all purposes to the same extent as if each individual publication or patent document were so individually denoted.

What is claimed is:

1. A compound derived from

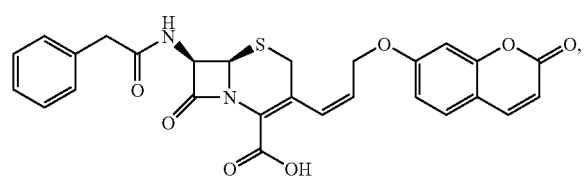

CC1 wherein the derived compound is esterified at the carboxyl moiety.

2. A compound derived from

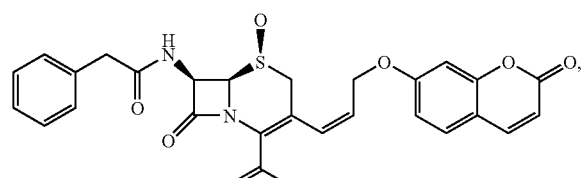

CC2 wherein the derived compound is esterified at the carboxyl moiety.

3. A compound derived from

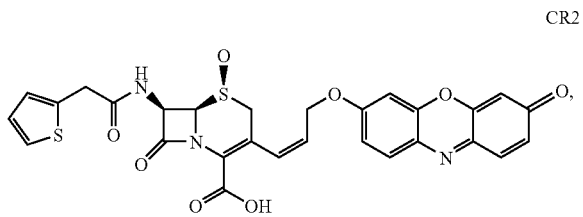

CR2 wherein the derived compound is esterified at the carboxyl moiety.

4. The compound

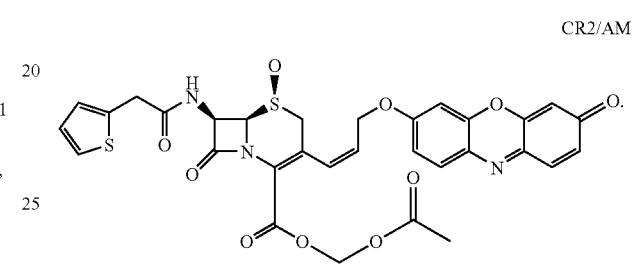

CR2/AM

5. The compound of claim 1, wherein the derived compound is a membrane-permeant derivative.

6. The compound of claim 2, wherein the derived compound is a membrane-permeant derivative.

7. The compound of claim 3, wherein the derived compound is a membrane-permeant derivative.

8. The compound of claim 1, wherein said compound is located within a living cell.

9. The compound of claim 2, wherein said compound is located within a living cell.

10. The compound of claim 3, wherein said compound is located within a living cell.

11. The compound of claim 4, wherein said compound is located within a living cell.

* * * * *